United States Patent
Gertner

(10) Patent No.: US 7,588,551 B2
(45) Date of Patent: Sep. 15, 2009

(54) HEMODIALYSIS ACCESS WITH ON-OFF FUNCTIONALITY

(76) Inventor: Michael Gertner, 520 Laurel St., Menlo Park, CA (US) 94025

( * ) Notice: Subject to any disclaimer, the term of this patent is extended or adjusted under 35 U.S.C. 154(b) by 0 days.

(21) Appl. No.: 11/734,186

(22) Filed: Apr. 11, 2007

(65) Prior Publication Data

US 2007/0249987 A1 Oct. 25, 2007

Related U.S. Application Data

(60) Continuation of application No. 11/425,106, filed on Jun. 19, 2006, which is a division of application No. 10/177,721, filed on Jun. 20, 2002, now Pat. No. 7,144,381.

(60) Provisional application No. 60/299,223, filed on Jun. 20, 2001.

(51) Int. Cl.
*A61M 5/00* (2006.01)

(52) U.S. Cl. .............. 604/9; 604/4.01; 604/16; 604/6.08; 604/5.01; 604/6.01; 604/19; 604/20; 604/21; 604/22; 604/27; 604/890.1; 604/891.1; 210/645; 210/646; 210/647; 210/696; 210/739; 210/746; 210/748

(58) Field of Classification Search ............... 604/4.01, 604/16.16, 6.08, 5.01–5.04, 6.16, 7.8, 19–22, 604/27, 890.1, 891.1; 210/645–647, 696, 210/739, 745, 746, 748, 194, 195.1–195.2, 210/252, 257.1, 257.2, 321.6; 600/437–439, 600/454, 458.9, 461.2, 464, 466–470, 11, 600/15; 606/1, 8, 10, 32–34, 108, 127, 128, 606/195, 110; 607/1–3, 44, 60, 61, 80, 88, 607/90, 94, 96–101, 104–106
See application file for complete search history.

(56) References Cited

U.S. PATENT DOCUMENTS 3,225,129 A 12/1965 Taylor et al.

(Continued)

FOREIGN PATENT DOCUMENTS

DE 24 07 559 7/1974

OTHER PUBLICATIONS

Arora, Pradeep et al.; "Hospital utilization among chronic dialysis patients", J. Am. Soc. Nephrology, vol. 11, pp. 740-746 (2000).

(Continued)

*Primary Examiner*—Tatyana Zalukaeva
*Assistant Examiner*—Ilya Y Treyger
(74) *Attorney, Agent, or Firm*—John P. O'Banion

(57) ABSTRACT

A treatment assembly is positioned along an AV-fistula and couples therapeutic energy to an adjacent area due to a material response to an applied energy field from a remotely located energy source. The treatment assembly may be delivered into the fistula through a hemodialysis needle, or may be secured to the fistula graft itself and implanted therewith within a patient. A cover provides a shield between an anastomosis area and blood flow. Another AV-fistula includes a valved reservoir that receives a fluid agent from a hemodialysis needle while moving the needle into or from the fistula; the agent leaks from the reservoir into the fistula lumen. Another valved fistula is adjustable between an open condition and closed conditions during and between hemodialysis treatments, respectively. Another AV-fistula has a bladder reservoir coupled to a second refillable fluid reservoir and is adapted to locally deliver a therapeutic agent into the fistula lumen.

14 Claims, 21 Drawing Sheets

U.S. PATENT DOCUMENTS

| | | | |
|---|---|---|---|
| 3,864,248 A | | 2/1975 | Granger et al. |
| 3,953,566 A | | 4/1976 | Gore |
| 3,962,153 A | | 6/1976 | Gore |
| 4,187,390 A | | 2/1980 | Gore |
| 4,220,153 A | | 9/1980 | Dresback |
| 4,230,119 A | * | 10/1980 | Blum ........................ 606/194 |
| 4,267,863 A | | 5/1981 | Burelle |
| 4,536,018 A | | 8/1985 | Patarcity |
| 4,647,378 A | | 3/1987 | Minami |
| 4,650,466 A | | 3/1987 | Luther |
| 4,662,383 A | | 5/1987 | Sogawa et al. |
| 4,787,921 A | | 11/1988 | Shibata et al. |
| 4,822,341 A | * | 4/1989 | Colone ........................ 604/175 |
| 4,828,544 A | * | 5/1989 | Lane et al. ..................... 604/9 |
| 4,967,765 A | | 11/1990 | Turner et al. |
| 5,391,197 A | | 2/1995 | Burdette et al. |
| 5,454,374 A | | 10/1995 | Omachi |
| 5,562,617 A | | 10/1996 | Finch, Jr. et al. |
| 5,571,169 A | | 11/1996 | Plaia et al. |
| 5,620,409 A | | 4/1997 | Venuto et al. |
| 5,690,115 A | | 11/1997 | Feldman et al. |
| 5,702,715 A | | 12/1997 | Nikolaychik et al. |
| 5,707,332 A | | 1/1998 | Weinberger |
| 5,769,870 A | * | 6/1998 | Salahieh et al. ............ 606/198 |
| 5,876,366 A | | 3/1999 | Dykstra et al. |
| 5,879,320 A | | 3/1999 | Cazenave |
| 5,902,336 A | * | 5/1999 | Mishkin .................. 623/11.11 |
| 5,911,704 A | | 6/1999 | Humes |
| 6,007,516 A | | 12/1999 | Burbank et al. |
| 6,019,788 A | * | 2/2000 | Butters et al. .............. 623/1.35 |
| 6,022,335 A | | 2/2000 | Ramadan |
| 6,037,329 A | | 3/2000 | Baird et al. |
| 6,076,529 A | | 6/2000 | Vanney et al. |
| 6,077,443 A | | 6/2000 | Goldau |
| 6,086,573 A | | 7/2000 | Siegel et al. |
| 6,102,884 A | * | 8/2000 | Squitieri ........................ 604/8 |
| 6,113,570 A | | 9/2000 | Siegel et al. |
| 6,153,252 A | | 11/2000 | Hossainy et al. |
| 6,165,196 A | * | 12/2000 | Stack et al. .................. 606/194 |
| 6,177,049 B1 | | 1/2001 | Schnell et al. |
| 6,200,256 B1 | | 3/2001 | Weinberger |
| 6,210,393 B1 | | 4/2001 | Brisken |
| 6,214,887 B1 | | 4/2001 | Cote et al. |
| 6,216,041 B1 | | 4/2001 | Tierney et al. |
| 6,217,503 B1 | | 4/2001 | Weinberger et al. |
| 6,231,587 B1 | | 5/2001 | Makower |
| 6,261,255 B1 | | 7/2001 | Mullis et al. |
| 6,308,737 B1 | | 10/2001 | Krivitski |
| 6,319,465 B1 | | 11/2001 | Schnell et al. |
| 6,323,184 B1 | | 11/2001 | Zalewski et al. |
| 6,361,531 B1 | | 3/2002 | Hissong |
| 6,387,116 B1 | | 5/2002 | McKenzie et al. |
| 6,398,764 B1 | | 6/2002 | Finch, Jr. et al. |
| 6,595,941 B1 | * | 7/2003 | Blatter ........................ 604/4.01 |
| 7,025,741 B2 | * | 4/2006 | Cull ............................... 604/9 |
| 2003/0100934 A1 | | 5/2003 | Stephens et al. |
| 2003/0163147 A1 | | 8/2003 | Rabiner et al. |

OTHER PUBLICATIONS

Stehmen-Breen, Catherine O. et al.; "Determinants of type and timing of Initial permanent hemodialysis vascular access", Kidney International, vol. 57, pp. 639-645 (2000).

Swapna, Joseph et al.; "Vascular access problems in dialysis patients", Heart Disease, vol. 3, pp. 242-247 (2001).

Tellis, Vivian A. et al., "Expanded polytetrafluoroethylene graft fistula for chronic hemodialysis", Ann. Surg., vol. 189, No. 1, pp. 101-105 (1978).

* cited by examiner

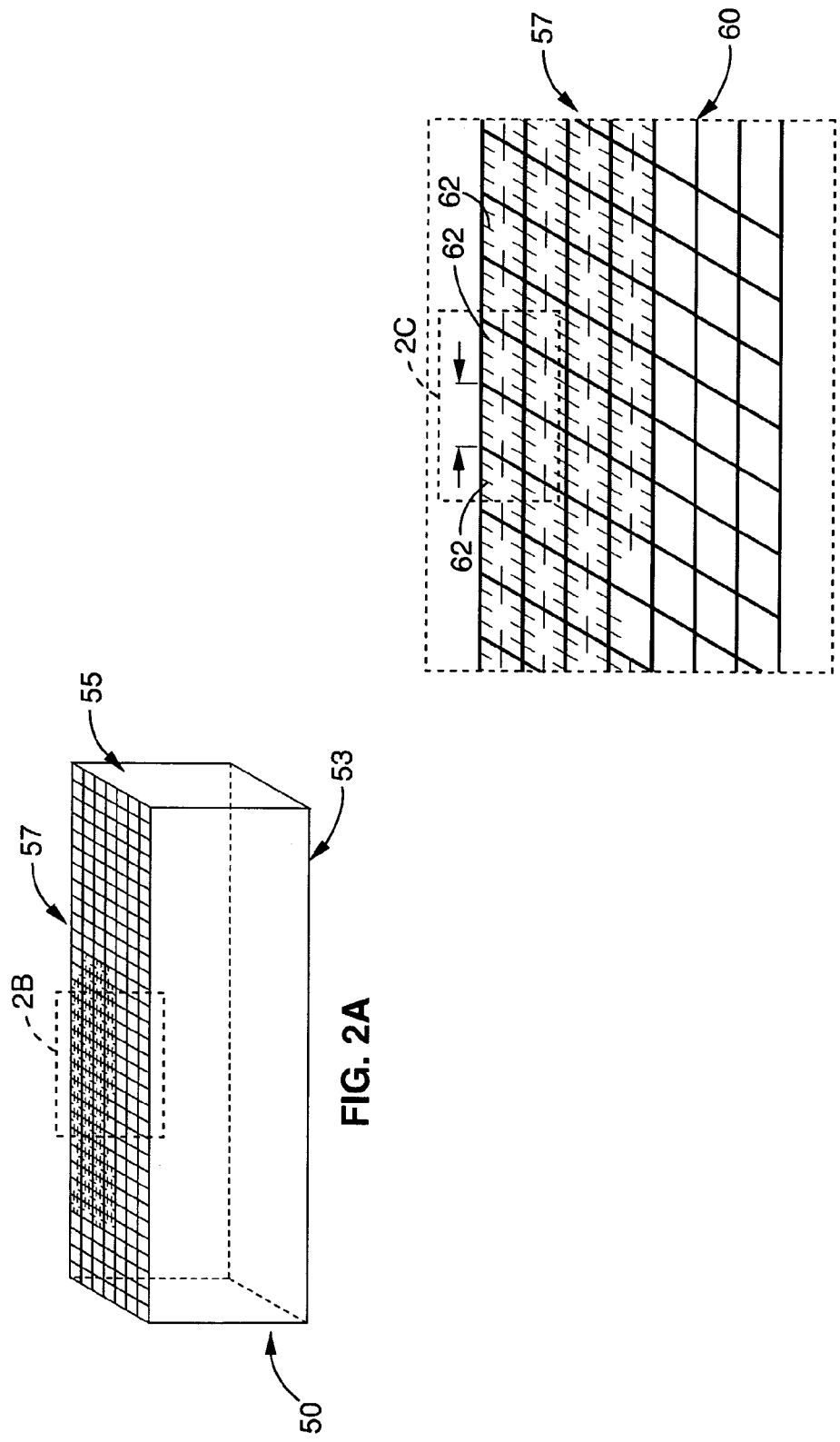

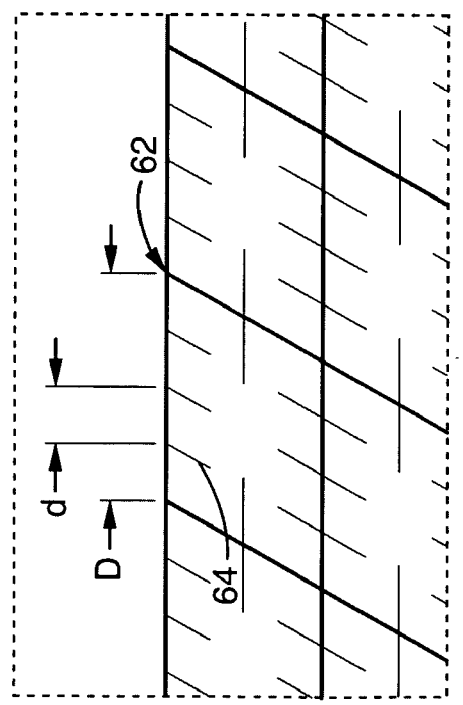
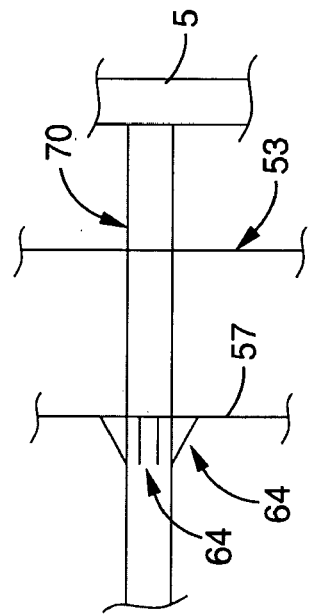
FIG. 2C
FIG. 2D

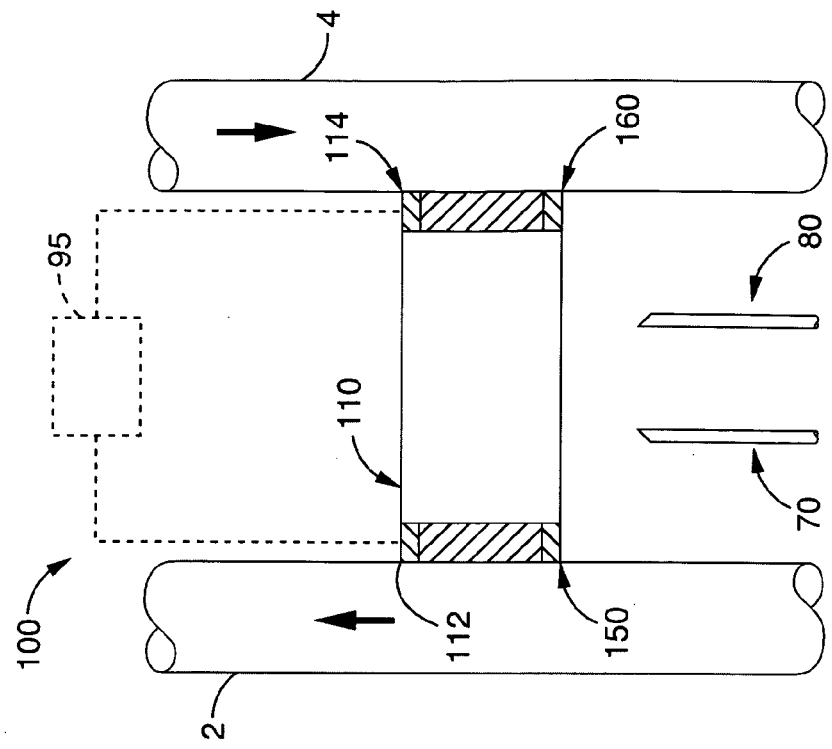
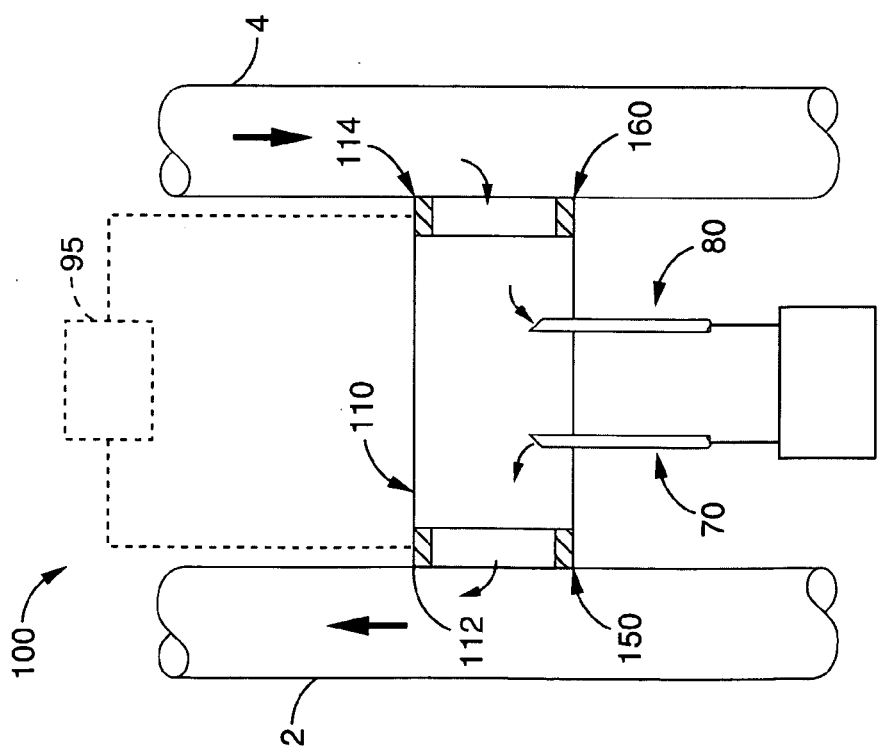
FIG. 3B
FIG. 3A

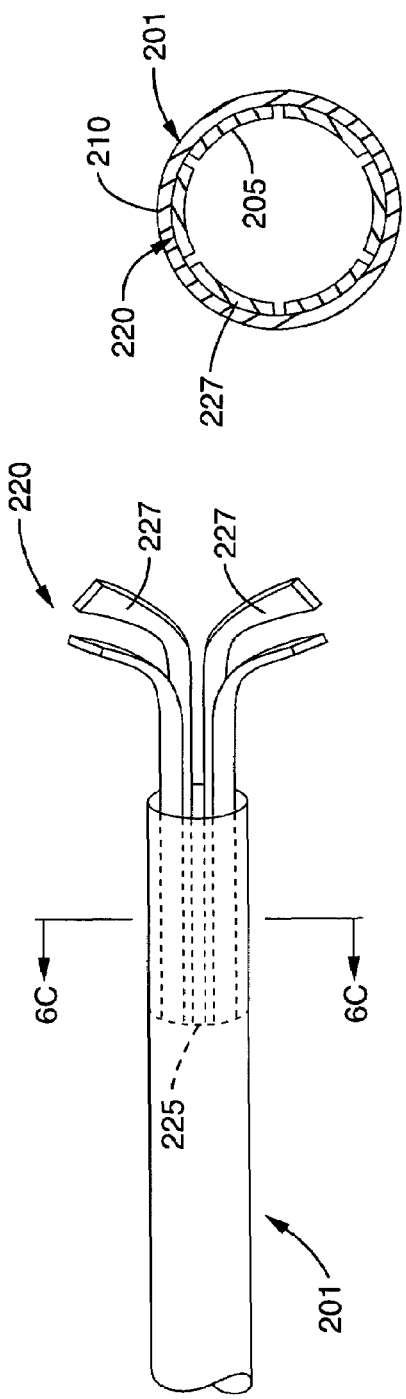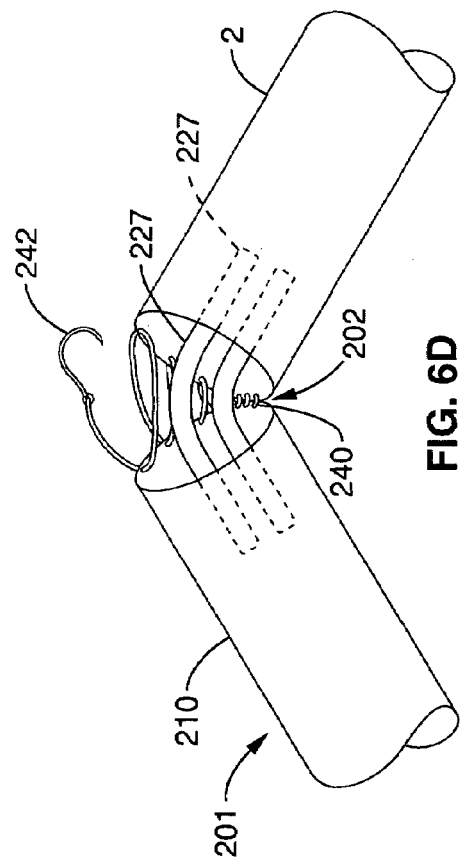

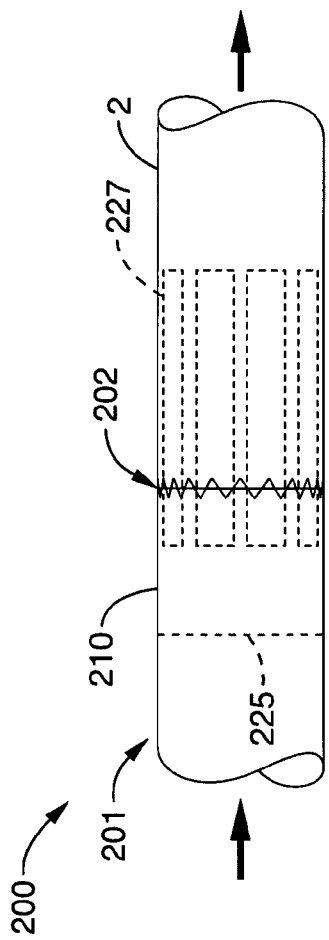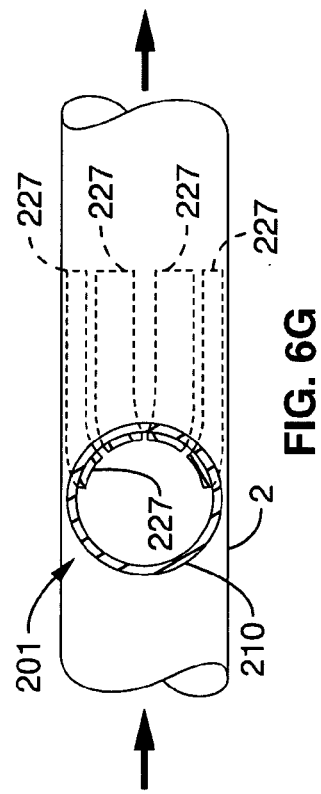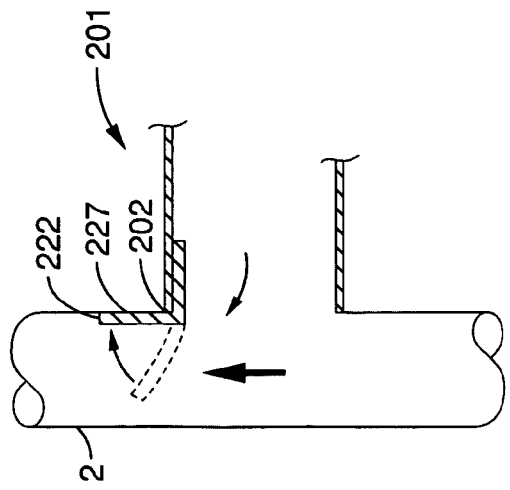

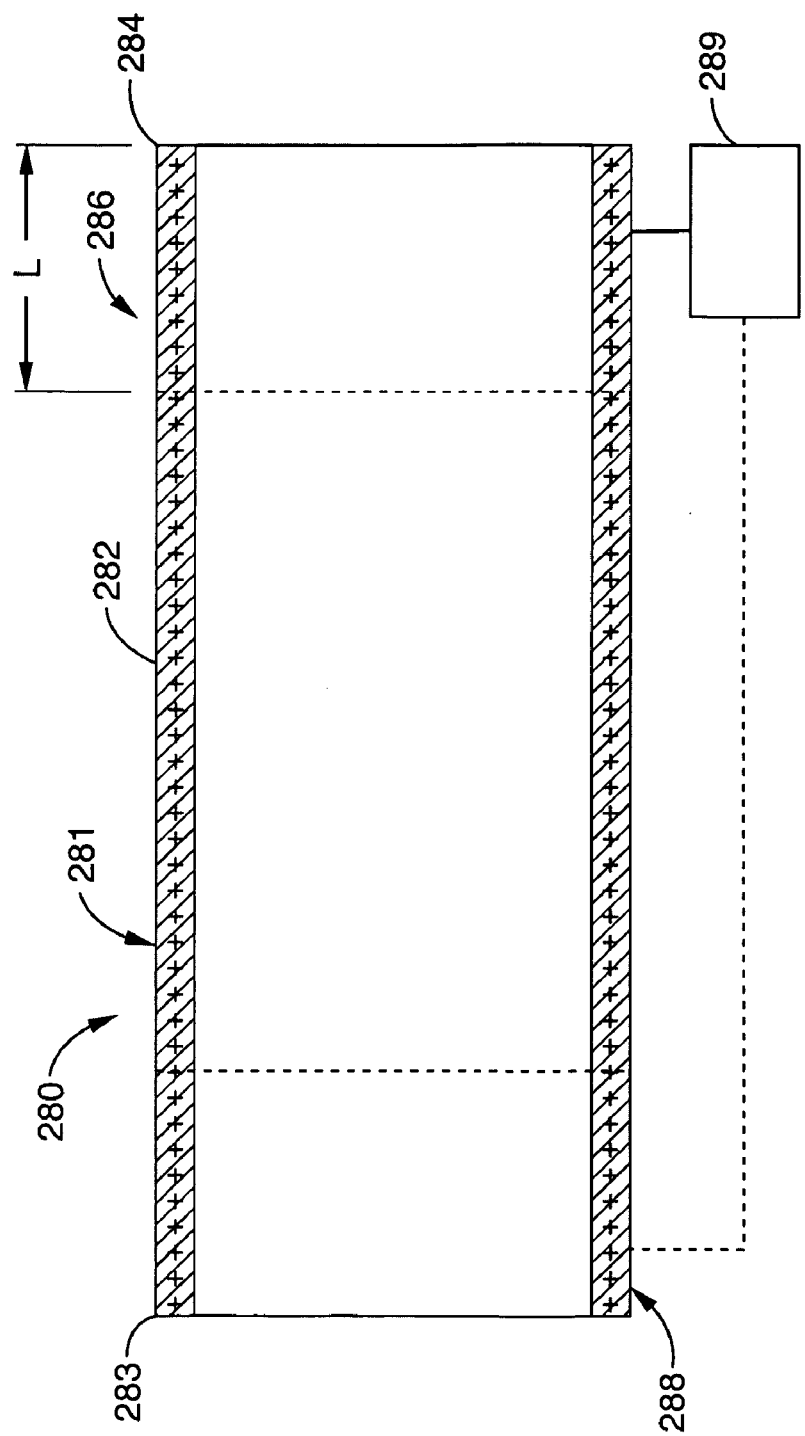

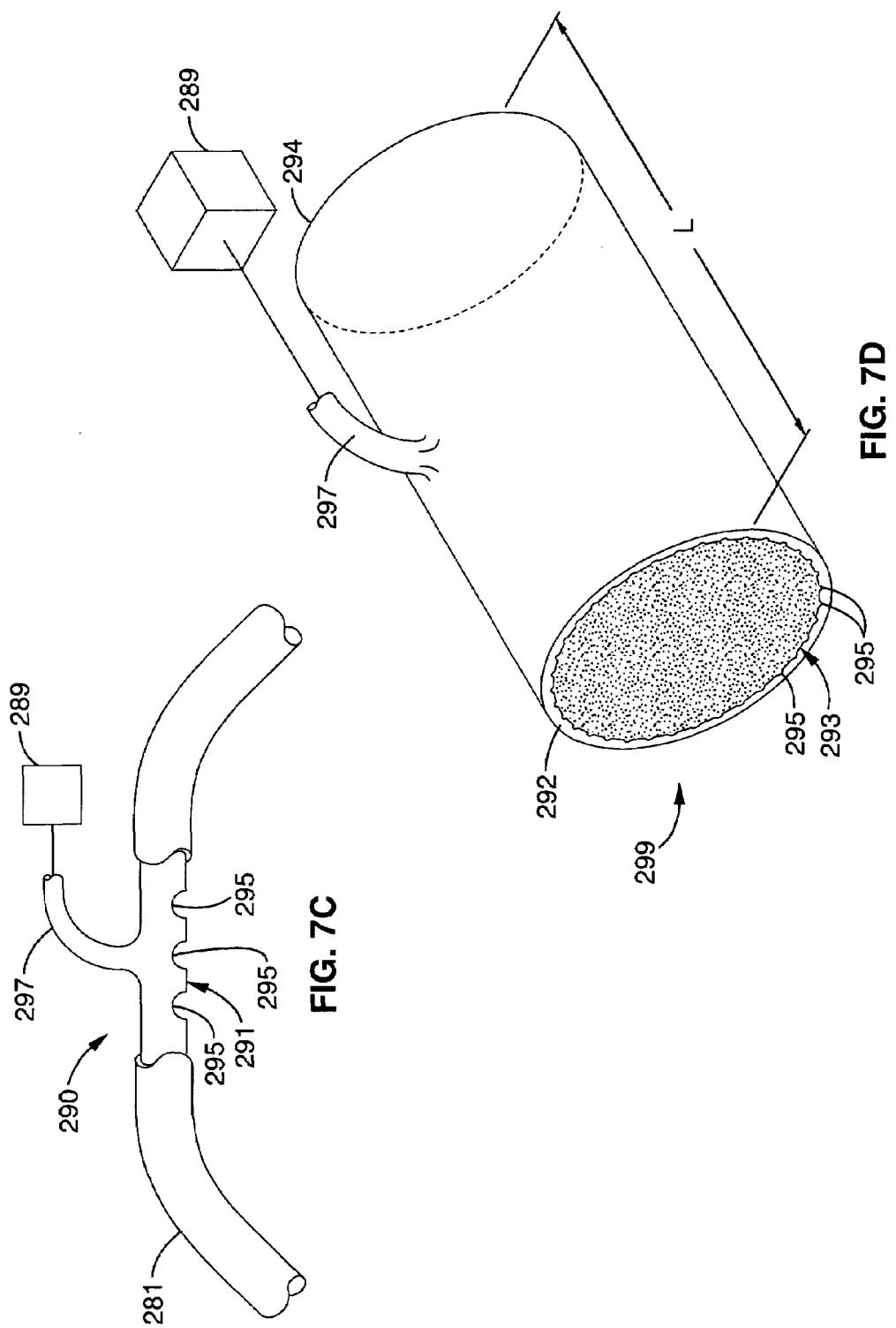

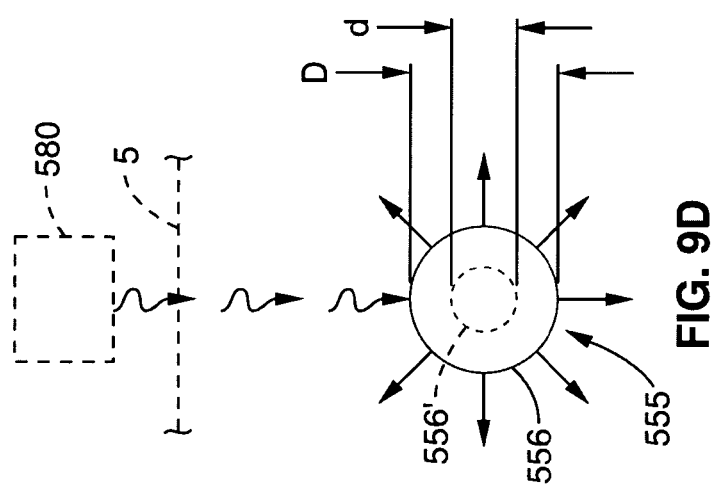

HEMODIALYSIS ACCESS WITH ON-OFF FUNCTIONALITY

CROSS-REFERENCE TO RELATED APPLICATIONS

This application is a continuation of U.S. application Ser. No. 11/425,106, filed on Jun. 19, 2006, incorporated herein by reference in its entirety, which is a divisional of U.S. application Ser. No. 10/177,721, filed on Jun. 20, 2002, now U.S. Pat. No. 7,144,381, incorporated herein by reference in its entirety, which claims priority from U.S. provisional application Ser. No. 60/299,223, filed on Jun. 20, 2001, incorporated herein by reference in its entirety.

This application is related to PCT International Publication No. WO 03/000314 A2, published on Mar. 1, 2003, incorporated herein by reference in its entirety.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention pertains generally to hemodialysis, and more particularly to hemodialysis systems and methods including A-V fistula grafts, A-V fistula graft treatment systems, systems for treating a condition associated with an AV-fistula graft, and an A-V fistula graft systems.

2. Description of the Background Art

Renal disease and deficiency has long been a significant problem that continues to plague an enormous population of patients, and the related cost of treatment continues as an ever growing burden on modern society as a whole. For example, in 1996, there were 250,000 patients in the US with end stage renal disease (ESRD), a number expected to grow by 10-15% per year over the next 20 years primarily as a result of an aging population and advances in treatments for other diseases. The cost of ESRD in the US was $20 billion in the year 2000, 5% of all Medicare resources.

Dialysis involves cannulation of the vascular system for extracorporeal flow of blood through a dialysis machine, which acts as a filter. To filter the blood efficiently, the dialysis machine requires 300-400 ml/min of flow for approximately three hours three times per week. To supply this high a flow rate, a large vein is required which will provide a flow rate of at least 300-400 ml/min. Otherwise, the vessel will collapse as the dialysis machine pulls out blood.

Various central venous devices and methods have been disclosed that provide this generally required level of flow. Examples of such devices include, without limitation, "TESSIO™" and "QUINTON™" catheters, which are commercially available from Medical Components and Kendall (owned by Tyco International) corporations, respectively. In general, these devices are inserted into the subclavian or internal jugular veins, communicate exteriorly of the patient, and at best are considered "semi-permanent" devices in that their longevity is limited, generally lasting up to a typical maximum of about 4 months.

The primary "long-term" solution generally involves gaining peripheral vessel access, most typically in an accessible region of a patient's arm. This generally requires a surgical procedure, wherein an artery is surgically attached to a vein, either directly or via an artificial conduit that creates an arterio-venous fistula, such as for example a conduit made from polytetrafluoroethylene (PTFE) or a woven polyester such as Dacron™. This procedure essentially short-circuits the normal blood path to the hand, and can provide a flow of approximately 1 liter/min. The conduit fistula is typically coupled to the corresponding arteries, such as by suturing, at locations called arterial and venous (respectively) "anastomoses". According to the typical dialysis procedure, the dialysis fistula is connected to a dialysis machine via dialysis needles that puncture the fistula conduit at a location between the anastomoses. Blood traveling from the fistula through the needles are carried by tubing into a dialyzer, which cleanses the blood by removing waste matter, and returns the blood via another needle to the fistula. A typical blood cleansing procedure lasts about 3 hours, after which the dialysis needles are removed and pressure is held at the site of needle entry. Most patients require dialysis about three times per week. A damaging process called "intimal hyperplasia" often begins at the time of surgery, and continues undisturbed in most cases until it leads ultimately to failure of the access fistula.

In common practice, an artificial conduit is used 70% of time, as has been previously disclosed by Stehman-Breen et al., "Determinants of type and timing of initial permanent hemodialysis vascular access," Kidney International, 57(2000) 639-645. However, about 50% of these grafts have been observed to malfunction within 2 years of implantation, as has been previously published by Diskin, C J et al., "Pharmacologic Intervention to Prevent hemodialysis Access Thrombosis," Nephron 1993:64(1-26). A study by Tellis, V. A. et al., "Expanded Polytetrafluoroethylene Graft Fistula for Chronic Hemodialysis," Ann. Surg., Vol 189(1), 1979, pp 101-105, revealed a 62% primary patency rate in PTFE grafts. It is not believed that this number has changed significantly since this study despite enormous advances in technology in other fields. The disclosures of the reference articles provided in this paragraph are incorporated herein in their entirety by reference thereto.

The creation of such a fistula increases flow to the arm and hence to the dialysis machine. The major problem in permanent dialysis access is the longevity of the fistula. With current methods, fistula survival is generally about 8-12 months with artificial conduits, and generally about 2-3 yrs with autogenous conduits. In fact, it is believed that about 3 "revision procedures" are required for every new fistula created. Each revision procedure requires a new access site on the patient's body. While the new fistula matures, a semi-permanent catheter needs to be placed in a large central vein. This usually leads to substantial morbidity, cost, and physician frustration; and in 1993 vascular access was described as a $1 billion problem. In a study published by Arora, P. et al., "Hospital Utilization among Chronic Dialysis Patients," J. Am. Soc. Nephrol., 11: 740-746, 2000, 36% of all hospital admission for dialysis patients was for matters related to access. Patients on dialysis require an average of about 2.2 hospitalizations and about 14.8 hospital days per year related to dialysis access. Many patients die secondary to lack of access. In an earlier study cited by Swapna, J. et al. in "Vascular Access Problems in Dialysis Patients," Heart Disease 2001; 3:242-247, about 18% of deaths in the dialysis population was due to lack of access. Though this number may have decreased in recent years as devices and techniques improve, it still remains a significant issue that deserves attention. The disclosures in the reference articles cited in this paragraph are herein incorporated in their entirety by reference thereto.

Morbidity related to fistulas fall into several categories, the most common of which (e.g. about 95%) is clotting of the graft. Infection occurs in 18% of complications and pseudoaneurysm in about 2%. The clotting pathophysiology can be further subdivided into clotting secondary to a venous stenosis (about 55% of cases), or secondary to an arterial stenosis (about 10% of cases). Other reasons for clotting include hypotension and pressure to curtail bleeding following a dialysis session.

Access to a fistula currently entails placement of a needle through the skin and into the fistula with subsequent attachment to a dialysis machine. The placement of the needle is not standardized with respect to the fistula, being placed in a different spot in the graft each time, resulting in disruption of the ultrastructure of the material over time. Twenty (20%) percent of fistula failures occur at the site of needle entry and manifest as thrombosis, pseudoaneurysms, and aneurysms. Furthermore, at least about 10 minutes of pressure is usually required to prevent hematoma formation at the access site, which may itself lead to a thrombosis.

Various devices and methods intended to treat AV-fistula stenoses with localized energy delivery have been disclosed. For example, several devices and methods have been disclosed for delivering ultrasound energy to an anastomosis region.

At least one example of this type is intended to deliver ultrasound energy to the area of an existing fistula thrombosis in combination with delivery of an echo contrast agent into the area to enhance the ultrasonic affects at the thrombosis. The ultrasound energy may be delivered transcutaneously to the area, or intravascularly such as by use of a miniature ultrasonic transducer located on a catheter inserted within the fistula. However, this particular technique suffers by the rapid clearance that the contrast agent may experience from the area in a blood flow environment. Also, this example does not provide for a device or method for using energy delivery for regular preventative maintenance of fistula patency, such as to prevent thrombus formation or adhesion in the fistula, or to prevent or treat neo-intimal hyperplasia.

At least one other example also includes a system and method for delivering ultrasound to the anastomotic junctions of fistulas in order to inhibit substantial neo-intimal hyperplasia by use of an ultrasound transducer located on an internal catheter probe within the fistula, or with a focused ultrasound transducer assembly associated with an external ultrasound energy source. However, this example does not provide for prevention or removal of thrombus. In addition, the internal catheter aspect of this example requires an active ultrasound energy source to be located on the catheter itself, which results in significant complexity and cost that may be prohibitive to regular maintenance use as a disposable assembly. The active source in addition may limit the ability to make such a catheter sufficiently small to be inserted into a fistula lumen through certain needles such as certain hemodialysis needles.

In addition to the limitations of the previous ultrasound energy delivery examples just described, they also do not provide for a system or method for actuating an treatment device within a fistula to deliver vibratory or other energy to tissues by exposing the treatment assembly to an applied energy field from a remotely located energy source outside of the fistula, such as externally of the patient and transcutaneously across a skin barrier. Nor do these previous techniques provide for the ability to deliver an energy delivery treatment assembly into a fistula through a hemodialysis needle such that additional punctures of the fistula are not required. Still further, these previous techniques also do not provide for an energy delivery treatment assembly secured to and implanted with a fistula graft. Nor do these techniques provide for other forms of energy delivery than ultrasound into problematic areas associated with fistula grafts in order to provide therapy to a patient.

Another example of a previously disclosed device system and method provides for delivery of a doppler ultrasound monitoring transducer into a fistula through a hemodialysis needle. However, the doppler device and method of this example does not deliver energy into the fistula in order to affect treatment or prevention of stenosis associated with the fistula. Other beneficial forms of energy delivery other than doppler ultrasound also are not provided according to this example. Moreover, there is no provision for applying an energy field from outside of a fistula to actuate energy delivery from a treatment assembly located within the fistula.

Various previous disclosures that provide additional background information and further illustrate the context of various aspects of medical device systems and methods herein summarized or described include the following issued U.S. Pat. No. 3,225,129 to Taylor et al.; U.S. Pat. No. 3,953,566 to Gore; U.S. Pat. No. 3,962,153 to Gore; U.S. Pat. No. 4,187,390 to Gore; U.S. Pat. No. 4,267,863 to Burelle; U.S. Pat. No. 4,536,018 to Patarcity; U.S. Pat. No. 4,787,921 to Shibata et al.; U.S. Pat. No. 6,019,788 to Butters et al; U.S. Pat. No. 6,102,884 to Squitieri; and U.S. Pat. No. 6,153,252 to Hossainy et al. The disclosures of these references are herein incorporated in their entirety by reference thereto.

Other previously disclosed devices and methods that disclose additional background information related to at least one of fistulas, valves, renal interventions, or dialysis may be reviewed by reference to the following issued U.S. Pat. No. 4,822,341 to Colone; U.S. Pat. No. 5,454,374 to Omachi; U.S. Pat. No. 5,562,617 to Finch et al.; U.S. Pat. No. 5,690,115 to Feldman et al.; U.S. Pat. No. 5,702,715 to Nikolaychik et al.; U.S. Pat. No. 5,879,320 to Cazenave; U.S. Pat. No. 6,086,573 to Siegel et al.; U.S. Pat. No. 6,113,570 to Siegel et al.; U.S. Pat. No. 6,177,049 to Schnell et al; U.S. Pat. No. 6,319,465 to Schnell et al.; and U.S. Pat. No. 6,387,116 to McKenzie et al. The disclosures of these references are also herein incorporated in their entirety by reference thereto.

Despite certain advances that may have been provided by various of the disclosures cited above, there are still many needs that have not yet been adequately met.

There is still a need for a hemodialysis system and method that provides for improved longevity and patency of AV-fistula implants.

There is in particular still a need for a hemodialysis system and method that substantially prevents or removes occlusive stenoses associated with AV-fistula implants.

There is also a need to accomplish the foregoing while minimizing morbidity and without the use of substantially invasive interventions.

There is also in particular a need to provide for routine, therapeutic energy delivery into localized areas associated with implanted fistulas using disposable energy coupling assemblies that are cost effective and that may be delivered using conventional hemodialysis needles.

BRIEF SUMMARY OF THE INVENTION

The present invention generally comprises hemodialysis systems and methods, including, without limitation, A-V fistula grafts, A-V fistula graft treatment systems, systems for treating a condition associated with an AV-fistula graft, and an A-V fistula graft systems.

One object of the invention is to provide a hemodialysis system that accomplishes the foregoing needs that have not been heretofore met by previously disclosed systems.

Accordingly, one aspect of the hemodialysis system includes at least one treatment assembly that is adapted to be positioned at a location along an AV-fistula graft implant extending between an artery and a vein. The treatment assembly is adapted to couple energy between the treatment assembly and an area adjacent to the treatment assembly sufficient to provide a therapeutic effect within the AV-fistula.

In one mode of this aspect, the treatment assembly is adapted to be located along an end portion of the AV-fistula graft that is adapted to be anastomosed between the artery or vein. According to one embodiment of this mode, the treatment assembly is adapted to be located along the position at a graft end portion that is anastomosed to the vein. In one further variation of this embodiment, the treatment assembly is adapted to be located at either of two positions along each of two respective graft end portions, respectively, that are adapted to be anastomosed to the vein and artery, also respectively.

In another mode, two treatment assemblies are provided and are adapted to be located along each of two end portions of the AV-fistula graft, respectively, that are adapted to be anastomosed to the vein and artery, also respectively.

In another mode, the treatment assembly is located along a distal end portion of an elongate body of a catheter device.

In one beneficial embodiment of this mode, the distal end portion and treatment assembly are adapted to be delivered to the location through a hemodialysis needle and into the graft extending between the vein and artery anastomoses.

In a further embodiment, the distal end portion is adapted to track over a guide wire to the location within the AV-fistula graft in-situ. In another embodiment, the distal end portion has a deflectable shape by manipulating a deflection member extending from a proximal end portion of the catheter body and the distal end portion.

In still a further embodiment of this mode, the treatment assembly has an expandable member that is expandable between a radially collapsed condition and a radially expandable condition. In the radially collapsed condition, the expandable member has a first outer diameter that is adapted to be delivered to the location within a lumen of the graft through the hemodialysis needle. In the radially expanded condition, the expandable member has a second larger outer diameter and the treatment assembly is adapted to couple energy to the area adjacent the expandable member in the expanded condition.

In one further variation of this embodiment, the treatment assembly is adapted to couple energy to a circumferential area surrounding the expandable member in the radially expanded condition. In another further variation, the expandable member is an inflatable balloon. One feature of the inflatable balloon includes a highly elastomeric material, which may be chosen in beneficial examples from polyurethane, silicone, or latex rubber, or combinations or blends thereof. In an alternative feature, the inflatable balloon is constructed of a relatively non-compliant material such that the balloon is folded in the radially collapsed condition.

In another mode, the treatment assembly is adapted to be implanted at the position along an AV-fistula graft.

According to one embodiment of this mode, the AV-fistula graft includes a graft body and the treatment assembly is adapted to be secured to the graft body at the location.

In one variation of this embodiment, the treatment assembly includes at least one member that extends beyond one of two opposite ends of the tubular graft body. According to one feature of this variation, the member is a tubular member secured to the graft body and extending beyond the end. According to another feature, the treatment assembly comprises a plurality of adjacent elongate members positioned around a circumference and extending longitudinally beyond the graft end. The members according to this feature are adapted to be positioned to cover the anastomosis between the graft body end and the respective artery or vein with respect to blood flow, and may be substantially pliable and deflectable under pressure of blood flow in order to cover the anastomosis region. A still further variation of this feature provides the members along only a portion of a circumference surrounding a longitudinal axis of the graft body, which portion may be located along a downstream side of an anastomosis between the graft and a vein or artery.

In another mode, the treatment assembly is adapted to be activated to couple the energy to the area by first coupling energy between the treatment assembly and a remotely located energy source. In one embodiment, the treatment assembly is adapted to heat upon the energy coupling with the energy source. In another further embodiment, the treatment assembly comprises a material that is adapted to receive energy from the energy source, which received energy activates the treatment assembly to couple energy between the treatment assembly and the area at the location. In one variation of this embodiment, the material is adapted to be ultrasonically actuated by a remote ultrasound energy source. In another variation, the material is a ferromagnetic material adapted to be inductively actuated under a magnetic field from the energy source. In another variation, the material is adapted to absorb light from a light energy source, such as in one further variation UV light. In still a further variation, the material is adapted to receive electrical current energy from the remotely located source.

In still another beneficial embodiment, the treatment assembly is adapted to couple energy from a remote energy source located across a skin layer of the patient when the treatment assembly is located at the position along the AV-graft fistula extending between vein and artery anastomoses within the patient's body.

In yet another mode, the system may further include the energy source in a combination kit with the treatment assembly.

In another mode, the device is adapted to couple a sufficient amount of energy between the treatment assembly and the area to substantially inhibit formation of a stenosis associated with the AV-fistula implant.

In a further mode, the device is adapted to couple a sufficient amount of energy between the treatment assembly and the area to substantially remove at least a portion of a stenosis associated with the AV-fistula implant.

In another mode, the treatment assembly is adapted to couple sufficient energy to the area to substantially prevent neo-intimal hyperplasia in the area.

In another mode, the treatment assembly is adapted to couple sufficient energy to the area to substantially prevent thrombogenesis or thrombus adhesion in the area.

In another mode, the distal end portion and treatment assembly is adapted to be delivered into the AV-fistula implant through a dialysis needle.

In another mode, the device is adapted to couple the energy between the treatment assembly and a substantially circumferential region of the AV-fistula circumscribing an internal lumen of the AV-fistula.

In another mode, the treatment assembly includes an adjustable member that is adjustable between a first shape having a first outer diameter that is adapted to be delivered into the AV-fistula, and a second shape having a second outer diameter that is greater than the first outer diameter.

According to one embodiment of this mode, the second outer diameter is sufficient to couple the energy between the adjustable member and a substantially circumferential region of the AV-fistula wall.

According to another embodiment of this mode, the adjustable member is a radially expandable member that is adjustable between a radially collapsed condition that characterizes the first shape and a radially expanded condition that characterizes the second shape.

In one further variation of this embodiment, the radially expandable member includes a radially expandable tubular member, which may beneficially have the feature of being an inflatable balloon. According to one highly beneficial version of this variation, the inflatable balloon is constructed from a highly compliant material, which further provides further benefits if provided with a material exhibiting at least 500% elongation between the radially collapsed and expanded conditions. Further exemplary embodiments providing such benefit may include a balloon made from at least one of the following materials: polyurethane; latex; silicone; or derivatives, combinations, or blends thereof. In a further version of the balloon variation, a valve assembly is provided that is adapted to allow the balloon to be inflated with fluid pressure provided by a hemodialysis needle. Such valve assembly may be beneficially positioned to allow such inflation during advancement of or withdrawal of the needle through the AV-fistula graft wall ancillary to a hemodialysis procedure.

In another mode, the treatment device is adapted to couple to an external energy source that is adapted to activate the treatment assembly in order to couple the energy between the treatment assembly and the area adjacent to the treatment assembly.

Another aspect of the invention provides a hemodialysis method that includes positioning a treatment assembly along a location of an AV-fistula graft extending between a vein anastomosis and an artery anastomosis, and coupling energy between the treatment assembly and an area adjacent to the treatment assembly such that a therapeutic or prophylactic affect is achieved within the AV-fistula graft.

In one mode of this aspect, the method includes first coupling energy from a remotely located energy source to the treatment assembly at the location, and then coupling energy between the treatment assembly and the area.

One embodiment of this mode includes coupling the energy between the energy source and the treatment assembly through tissue and without physically connecting the energy source and the treatment assembly.

Another embodiment of this mode includes coupling the energy between the energy source and the treatment assembly across a skin layer of the patient. In another embodiment considered highly beneficial, the method includes heating the treatment assembly with the energy coupled from the energy source, and thermally coupling the treatment assembly with the area. In certain further beneficial variations of these embodiments, the method may further include coupling ultrasound, light, inductive, or electrical energy between the energy source and the treatment assembly.

Another mode of this aspect includes implanting the treatment assembly at the location. One beneficial embodiment of this mode includes extending the treatment assembly beyond an end of the AV-fistula graft, and substantially covering an anastomosis region between the graft end and a respectively anastomosed region of vein or artery wall with respect to blood flow.

Another mode of this aspect includes delivering the treatment assembly to the location through a hemodialysis needle. One embodiment of this mode includes expanding an expandable member of the treatment assembly at the location and coupling energy between the expandable member and the area adjacent thereto.

Another mode of this aspect includes coupling sufficient energy between the treatment assembly and the area to substantially prevent formation of a stenosis at the location.

Another mode of this aspect includes coupling sufficient energy between the treatment assembly and the area to substantially reduce a stenosis at the location.

Another mode of this aspect includes coupling sufficient energy between the treatment assembly and the area to substantially prevent localized thrombus formation or adhesion at the location.

Another mode of this aspect includes coupling sufficient energy between the treatment assembly and the area to substantially reduce a localized thrombus at the location.

Another aspect of the invention is a hemodialysis system with an AV-fistula graft that includes a valve system coupled to a lumen of the AV-fistula graft and is adjustable between an open condition and a closed condition with respect to the lumen. In the open condition, the AV-fistula graft is substantially adapted to allow substantial fluid communication between an arterial and a venous anastomosis. In the closed condition, the fluid communication between the anastomoses is substantially occluded.

According to one mode of this aspect, the valve system includes at least one valve with an expandable member coupled to the AV-fistula lumen and that is adjustable between a radially collapsed condition and a radially expanded condition. The radially collapsed condition characterizes at least in part the open condition for the valve system and allows for fluid communication between the anastomoses. The radially expanded condition characterizes at least in part the closed condition for the valve system and substantially occludes the fistula lumen. In one embodiment of this mode, the expandable member is an inflatable balloon. In one variation of this embodiment, the valve system includes an inflation chamber that is adapted to allow the inflatable balloon to be inflated with pressurized fluid from a hemodialysis needle positioned within the inflation chamber. In another further variation, the inflation chamber is positioned to allow the hemodialysis needle to inflate the balloon without requiring an additional graft puncture with the hemodialysis needle before or after performing hemodialysis with the needle through the graft.

In another mode, the valve is located along an end portion of the AV-graft fistula that is adapted to be anastomosed to a blood vessel.

In yet another mode, the valve is located along an intermediate region of the fistula graft between the two end portions adapted to be anastomosed between an artery and a vein, respectively.

In still another mode, the system includes two valves positioned along two opposite ends, respectively, of the AV-fistula graft that are adapted to be anastomosed to an artery and vein, also respectively. In one embodiment, the two valves are adapted to independently adjusted between the respective open and closed conditions. In another alternative variation, they are adapted to be adjusted together with a common actuator.

Another aspect of the invention is a method for adjusting an AV-fistula graft between an open condition and a closed condition. In the open condition, the AV-fistula graft allows substantial fluid communication between the arterial and venous anastomoses. In the closed condition, the AV-fistula graft substantially prevents fluid communication between the arterial and venous anastomoses.

Another aspect of the invention is an AV-fistula graft that is adapted to locally deliver a therapeutic fluid agent into a tissue area adjacent to the graft when it is implanted between arterial and venous anastomoses.

According to one mode of this aspect, the graft includes a reservoir that is adapted to house the fluid agent and to elude the agent into the area.

In one embodiment, the reservoir is a bladder assembly associated with a graft body extending between the anastomoses. In one variation, the bladder assembly is an annular shape circumscribing the graft lumen and is adapted to deliver the agent into the graft lumen. In a further variation, the annular bladder includes pores located to deliver the agent into the lumen.

In another embodiment, the reservoir is adapted to be fluidly coupled to a remotely located fluid source and to receive fluid agent from the source for delivery into the lumen. In one variation, the system includes the remotely located fluid source. In a further variation, the fluid source is adapted to be implanted within the body of the patient. In another further variation, the fluid source is adapted to be refilled, such as with a syringe through a valve member associated with the fluid source. In another further variation, the fluid source is adapted to be located externally of the patient's body.

Each of the various aspects provided above are considered to be independently beneficial aspects of the invention, and is not required to be combined with the various other aspects or additional modes, embodiments, variations, or features provided. Notwithstanding the foregoing, the various combinations and sub-combinations of such aspects and additional modes, embodiments, variations, and features also provide further benefits and are thus considered to provide additional, independent value as would be apparent to one of ordinary skill based upon review of the totality of this disclosure as provided below and in the claims.

BRIEF DESCRIPTION OF THE DRAWINGS

FIG. 2A shows an angular perspective view of one particular valve assembly that is adapted for use with an AV-fistula in a hemodialysis system such as that shown in FIGS. 1B-D.

FIG. 2B shows an exploded top view of region 2B shown in FIG. 2A.

FIG. 2C shows an exploded top view of region 2C shown in FIG. 2B.

FIG. 2D shows a schematic side view of a hemodialysis needle positioned across a skin layer and through a valved assembly similar to that variously shown in FIGS. 2A-C.

FIG. 3A shows a schematic view of similar anatomy to that shown in FIGS. 1A-D, except shows the anatomy undergoing treatment with another hemodialysis system according to the invention with two valves coupled to the AV-fistula at respective locations adjacent to the fistula's anastomoses with the vein and artery, respectively, wherein the system is shown in one mode with both the valves in an open condition.

FIG. 3B shows a similar schematic view of the same anatomy and system as that shown in FIG. 3A, except shows the system in another mode with both valves in the respective closed conditions.

FIG. 6B shows an angular perspective view of one end of another AV-fistula embodiment according to the invention.

FIG. 6C shows a transverse cross-sectioned view taken along line 6C-6C in FIG. 6B.

FIG. 6D shows an angular perspective view of an AV-fistula of the invention similar to that shown in FIGS. 6B-C in one mode of use during an end-to-end anastomosis procedure with a vein.

FIG. 6E shows a side perspective view of the AV-fistula and vein shown in FIG. 6D after a completed end-to-end venous anastomosis.

FIG. 6F shows partially cross-sectioned side view of a further variation of an AV-fistula such as that shown in FIGS. 6B-F, and shows the fistula after a completed "side" anastomosis with a vein shown schematically.

FIG. 6G shows a partially cross-sectioned top view of the AV-fistula and anastomosed vein shown in FIG. 6F.

FIG. 7B shows a schematic view of another hemodialysis system according to the invention with an AV-fistula that is fluidly coupled to a remotely located fluid agent reservoir and locally administering fluid agent from the reservoir into the AV-fistula lumen.

FIG. 7C shows a partially segmented side view of one beneficial variation for the AV-fistula shown in FIG. 7B that includes an annular, porous bladder located within a graft wall of the AV-fistula.

FIG. 7D shows an exploded angular perspective view of a further porous bladder variation adapted for use in an AV-fistula embodiment similar to that shown in FIG. 7C.

FIG. 9D shows a schematic view of a transverse cross-section through a treatment device, such as provided by the catheter shown in FIGS. 9A-C, taken through an expandable member in a radially expanded condition, and shows in shadow the expandable member in a radially collapsed condition, and also schematically illustrates various aspects of energy coupling between the expandable member and an external energy source as well as with surrounding tissues.

DETAILED DESCRIPTION OF THE INVENTION

Figure 1B:
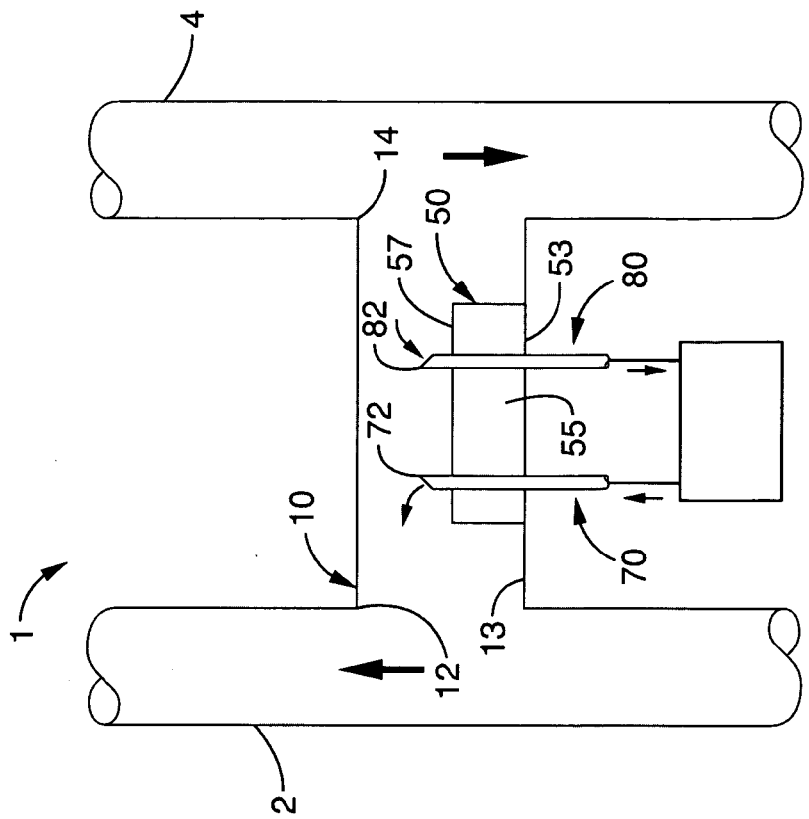
FIG. 1B shows a schematic view of the same regions of artery and vein as shown in FIG. 1A, except shows the artery and vein during one step of a hemodialysis procedure using a hemodialysis system according to the invention that includes an AV-fistula with a valve assembly in combination with hemodialysis needles extending through the valve assembly and into the fistula.
Figure 1A:
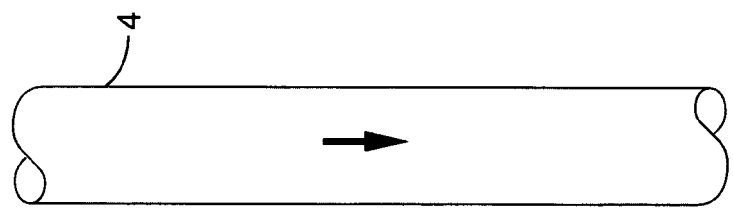
FIG. 1A shows a schematic view of certain corresponding regions of an artery and a vein of a patient prior to anastomosing an AV-fistula to those respective regions according to an initial stage of performing a hemodialysis procedure.
Figure 1A:
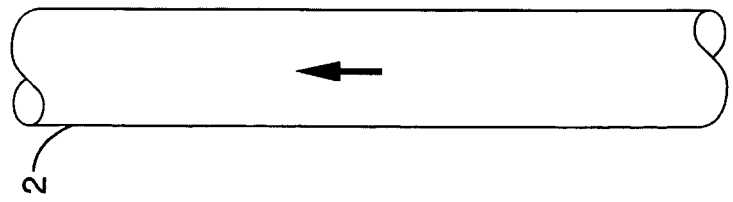

It is to be appreciated that the present invention in one regard provides a system with at least one device that is adapted to increase the long-term patency for an AV-fistula, and therefore longevity of dialysis access, with respect to a vein 2 and artery 4 in a patient, which are shown in FIG. 1A for the purpose of reference prior to beginning a hemodialysis procedure with the system and method of the present invention.

AV-Fistula With Valved Needle Access & Controlled Drug Delivery

Figure 1C:
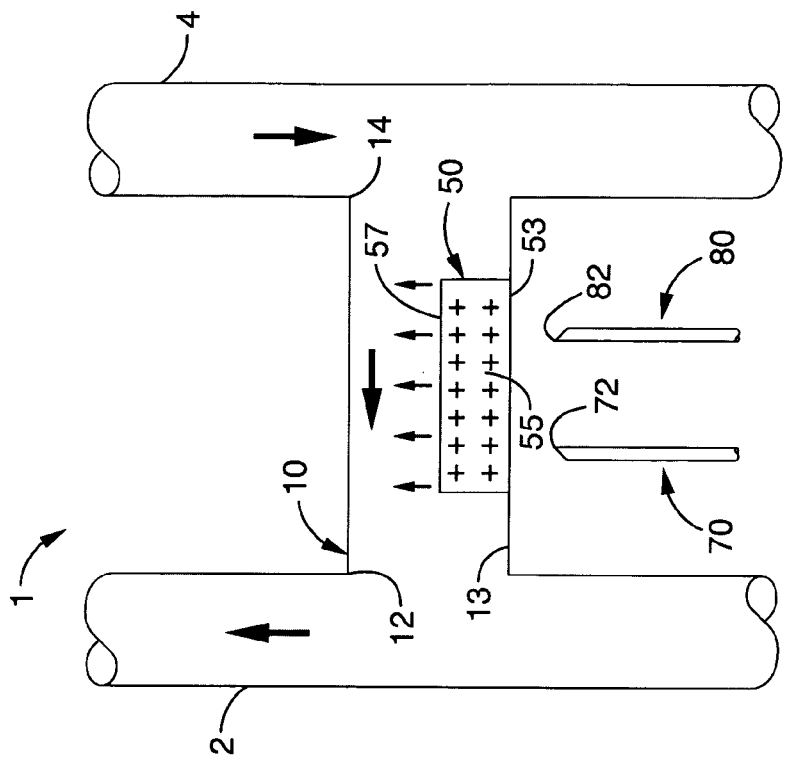
FIG. 1C shows a schematic view of the same anatomy and hemodialysis system as shown in FIG. 1A, except shows the hemodialysis system during another mode of use for providing a therapeutic agent to the AV-fistula contemporaneous with or in between hemodialysis procedures.
Figure 1D:
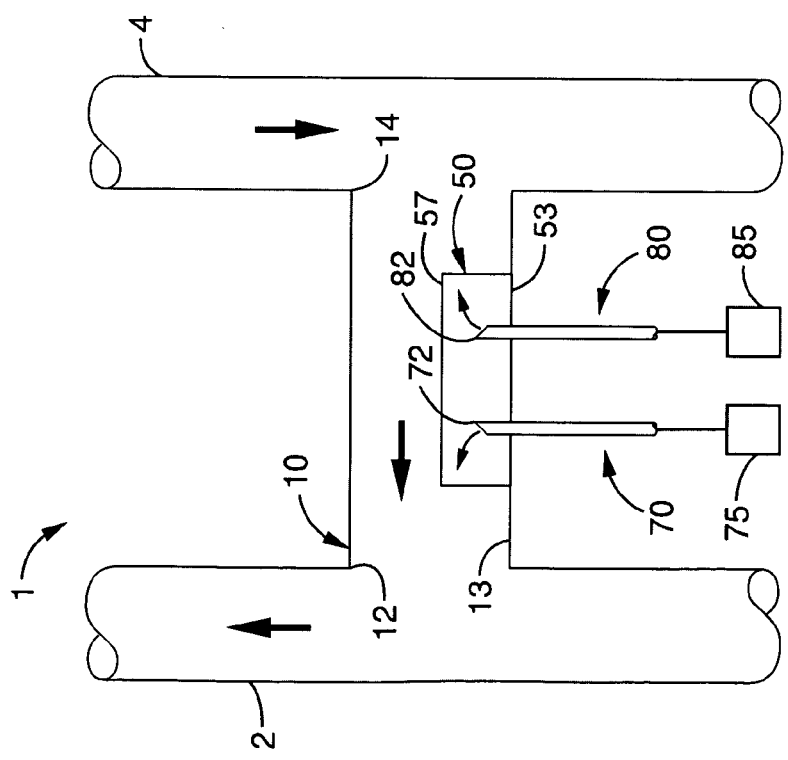
FIG. 1D shows a schematic view of the same anatomy as shown in FIG. 1A-C, and including the same AV-fistula with valve assembly shown in FIGS. 1B-C, except showing the valve assembly after removal of the hemodialysis needles from the fluid agent reservoir that allows for controlled delivery of the fluid agent contents into the lumen of the AV-fistula.

According therefore to one beneficial embodiment, FIGS. 1B-D show one hemodialysis system 1 of the invention with an AV-fistula 10 that extends between two anastomosis sites 12, 14 along vein 2 and artery 4, respectively. Along a wall of fistula 10, and generally flush with an outer surface thereof, is a localized valve system 50.

Valve system 50 may be integrated into fistula 10, such as in a pre-packaged, sterilized assembly. However, it is further contemplated that valve system 50 may also be provided separately. In this variation (not shown), the valve may be manually inserted through an aperture formed in the graft wall of the fistula, which aperture may be itself provided by the graft supplier or may be formed by the end user such as during initiation of the surgical procedure to create the AV-fistula. Per the latter example, this allows the positioning of the valve assembly to be customized by the user to meet the anatomic needs of a particular patient, or according to the preference of the particular healthcare provider performing the fistula implantation (or otherwise the hemodialysis procedure). Moreover, it is also to be appreciated that the present system 1 is principally adapted for use with an artificial conduit; however, in certain limited instances it may be further adapted for use in an autogenous fistula.

In any event, valve system 50 has two components: a first valve assembly that is generally a membrane 53, which sits above a second valve assembly 57 and demarcates a small reservoir 55. The cavity of reservoir 55 according to one particular embodiment contains a bioactive fluid agent, such as for example an antithrombotic, anti-mitotic, anti-proliferative agent, or combination of one agent with another pharmaceutical or agent, both of which will preferably leach from reservoir 55 and out into lumen 13 in-between dialysis sessions.

As shown in FIGS. 1C-D, the reservoir 55 may be filled with fluid agent by use of the dialysis needles 70, 80, such as during partial proximal withdrawal after hemodialysis so that the fluid ports in the needle tips 72, 82, respectively, are located within reservoir 55. This allows for delivery of the fluid agent without any additional intervention or venous (or arterial) puncture beyond what is already being done for the hemodialysis. In addition, needles 70, 80 may inject the agent from syringes or other pressurizeable source, such as is shown at sources 75, 85, respectively, which may be coupled to the syringes via a side arm while the syringes are also coupled to the hemodialysis machine, or separately coupled. Or, the hemodialysis machine may itself be adapted to provide the fluid agent delivery to the needles.

Moreover, it is further contemplated that the fluid agent solution may also be refilled in between dialysis sessions. In any case, many different elution profiles may be acceptable into lumen 13, depending upon the particular need for a fluid agent, lumen diameter, fistula dwell-time, inter-treatment periods, etc. In many cases, however, the elution profile would be a slow leak rate of the pharmaceutical through the valve, over the 2-3 days between dialysis. As such, the mechanism by which such "controlled" elution is achieved should be tailored to accomplish this objective according to the particular agent to be delivered. For example, a porous membrane may be provided integral with valve assembly 57, or along another wall bordering reservoir 55. Or, valve assembly 57 may not completely seal shut after it is opened to pass needles 70, 80 during dialysis. A controlled "leaky" valve may be sufficient to achieve the desired results. However, as valve assembly 57 is localized along fistula 10 in order to provide for standardized needle puncture site, drug delivery from reservoir 55 may not be accomplished along other portions of fistula 10 if done only through valve system 50. For this reason, reservoir 55 according to further embodiment may be adapted to couple its contents to regions of fistula 10 other than only where valve system 50 is located.

In use according to the present embodiment, fistula 10 and valve system 50 are surgically implanted beneath a patient's skin. Trained personnel would locate the valve system 50 in the fistula 10 via light touch and insert a dialysis needle through the skin and then through the top membrane in the valve assembly. Next, the needle would be further inserted through the valve and into the blood flow of the fistula. The same would be done for the second cannula. The result is shown in FIG. 1B.

At the end of the dialysis session, the needles are removed. As each individual needle is removed, a pharmaceutical solution is injected into the space between the membrane and the valve. This is shown in FIG. 1C, with one schematic view of the result shown in FIG. 1D for the purpose of further illustration.

According to this embodiment, bioactive fluid agent may be delivered into a localized reservoir associated with the fistula implant and by way of the hemodialysis needles, and such agent may then be delivered into the fistula lumen over a delayed period of time. Such system and method is highly beneficial for use with certain agents that are adapted to prevent clotting, infection, and neointimal hyperplasia, or to remove or dissolve the same. Further examples of such fluid agents that are applicable to the present embodiment, and to other embodiments herein shown or described where appropriate, include, without limitation: Cisplatin™; rapamune (or Rapamycin™); pacliitaxel (or Taxol™); heparin; hirudin; hirulog; exochelin; aspirin; streptokinase; urokinase; TPA; or derivatives, combinations, or blends thereof.

It is also to be appreciated that, though various of the embodiments for local agent delivery are beneficially adapted for coupling and delivery of fluid agents, such embodiments may also be adapted to store and/or deliver agents in other forms than fluid, such as for example powder or gel suspension forms. For example, delivery of a powder agent within a reservoir couple to a flow lumen of a fistula may be accomplished according to certain of the present embodiments without departing from the scope of the invention.

FIGS. 2A-D show further details of one particular embodiment for valve assembly 57 by reference to valve system 50 and adapted for use in an AV-fistula such as according to system 1 as follows.

Valve assembly 57 includes a wall 60 with a matrix or plurality of valves 62 that form a patterned grid, as shown in FIG. 2A and in increasing more detail in FIGS. 2B-D, respectively. More specifically, each valve 62 includes a plurality of moveable members 64 that are generally splines or struts and are adjustable between a first condition or position and a second condition or position. The first condition is characterized by the members 64 being in a first position and characterizes the closed condition for the valve 62 and is generally a resting condition, shown in FIGS. 2B-C. The second condition is characterized by the members 64 in second relative positions and characterizes the open condition for the valve 62 and characterizes the open condition, allowing a needle to pass therethrough (shown in FIG. 2D). In the particular embodiment shown and by reference to FIG. 2D, needle 70 passes through skin layer 5, then through first valve assembly or membrane 53 and second valve assembly 57. When passing through second valve assembly 57, the members 64 are adjusted from the closed condition to the open condition under force from advancing needle 70 against splines 64. Members 64 are sufficiently resilient such that subsequent withdrawal of needle 70 results in members 64 returning substantially back to their relative first positions, and thus substantially returning the valve 62 to the closed condition.

While various specific variations for valves 62 may be acceptable, further more detailed features which are believed to be acceptable are as follows. Members 64 are constructed of a superelastic metal alloy, such as a nickel-titanium alloy, and more particularly Nitinol™. Members 64 are formed from an initial foil or starting "blank" of the alloy material which is then processed to form members 64 in the integrated mesh shown, such as for example by photo etching, laser etching, or other suitable techniques. A typical starting foil may be between about 0.25 and about 0.5 millimeters thick, with resulting matrix having the following dimensions: width D of each valve being between about 1.25 and about 1.5 times the size of the dialysis needle to be used therethrough, which needles often will be between about 1 and about 1.5 millimeters in diameter; the spacing d between members 64 are generally between about 50 and about 500 microns.

Members 64 may also be coated with a coating. In one regard, a coating may be adapted to aid in preventing influx of blood factors into reservoir 55. Use of a hydrophobic coating, such as for example PTFE, may provide this result by surface tension effects through the gaps. Alternatively, a hydrophilic coating such as hydrogel may actually absorb water components from the blood pool or from the fluid in reservoir 55. Upon such absorption the coating swells and functionally "closes the gaps" without significantly degrading the available flexibility and therefore deflectability of members 64 as they are adjusted to their respective open positions under the force of the advancing needle.

It is to be appreciated that small gaps may remain between members 64, which may be designed for optimized drug elution from reservoir 55 into the graft lumen but resistance to blood factor influx. Therefore, the dimensions provided above may be adjusted according to the overall affect desired, and including with respect to the coating chosen for a particular assembly.

FIGS. 2A-D represent one beneficial embodiment for the valve assembly shown schematically in FIGS. 1A-D. However, despite the particular benefits of this embodiment, other alternative embodiments and variations are contemplated, and the intended scope of the invention should in one regard be considered broadly. For example, in one regard the valves 62 are generally considered to include a moveable member that is adapted to be moved from a first position to a second position by advancing a hemodialysis needle therethrough. In the first position, the valves 62 are closed and reservoir 55 is substantially sealed from blood leaking from lumen 13 of fistula 10. However, as mentioned above, such first position may be incomplete just enough to allow for drug elution from reservoir 55 and into lumen 13. In the second position shown, needle 70 passes into lumen 13 for hemodialysis treatment to be performed. These beneficial aspects need not be limited to the specific grating/cooperating spline embodiments shown, though they are in particular considered beneficial. In fact, single panes of alloy may replace the plurality of splines for each of the plurality of valves 62, and swing like a door between the open and closed conditions. Or, rather than square shaped arrangements for valves 62, circular shapes may be used, such as by providing a plurality of pie-shaped windows that cooperatively adjust between open and closed positions to open and close the valve. Substantially elastic memory polymers may be used instead of superelastic metal alloy, or other metals such as stainless steel may be used so long as the deflection does not result in such plastic deformation that a seal can not be adequately achieved after repeat use. Or, other mechanisms such as deflectable seated ball bearing valves, hydraulic bladders, compressible annular members, or self-sealing membrane materials (such as used for valve assembly 53, etc. may be used in certain circumstances.

AV-Fistula With Adjustable Valve System

The embodiments shown in FIGS. 3A-4D generally relate to an AV-fistula with a valved inner lumen, such that the fistula may be provided in an open condition during dialysis, but in a closed condition between dialysis procedures.

Figure 3C:
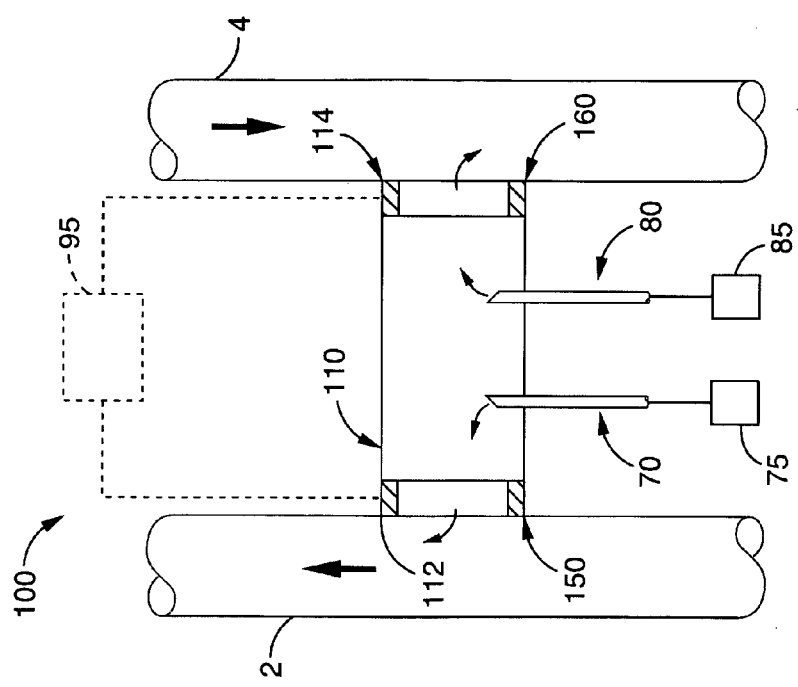
FIG. 3C shows a similar schematic view of the same anatomy and system as that shown in FIGS. 3A-B, except shows the system in another mode of use.

In the specific embodiment shown in FIGS. 3A-C, two valves 150, 160 are located along the two opposite end portions 112, 114, respectively, of fistula 110 that are anastomosed to vein 2 and artery 4, also respectively.

According to use of these valves 150, 160, the entire fistula 110 can be turned "on" and "off", or "open" and "closed", respectively, during and after (also respectively) dialysis sessions as follows.

When both valves 150, 160 are in the open condition, blood may flow between fistula 110 and both vein 2 and artery 4 and into properly placed needles 70, 80 for performing hemodialysis. This is shown in the configuration of FIG. 3A. However, when both valves are adjusted to the closed condition, as shown in FIG. 3B, blood is prevented from flowing from either vein 2 or artery 4 and into a substantial portion of fistula 110. Accordingly, thrombosis, "steel" hand, and cardiac output concerns that are often associated with the chronic shunting through long-term, indwelling AV-fistula's are mediated by the ability to prevent the shunt flow between hemodialysis procedures.

However, it is generally desired to remove blood from the region of fistula 110 located between valves 150, 160 in the closed condition over any substantial period of time, as a static reservoir is formed there that could result in significant clot formation. Accordingly, the region may be purged of blood and replaced by other agent from needles 70, 80. One mode forces blood out of fistula through open valves 150, 160, as shown in FIG. 3C. Another mode closes one valve, such as valve 150 adjacent vein 2, and then purges the fistula blood into artery 4 prior to closing valve 160 in a subsequent step; or, the opposite order of valve closing may be pursued, such as shown in FIG. 4D including phantom view of valve 160 (further described below). In addition, with both valves 150, 160 closed, by providing a vacuum suction to lumen 133, allows lumen 133 to be evacuated, and according to suitable level of vacuum and structure for wall 131 allows member 130 to collapse in an evacuated condition between treatments. Or, both valves can be closed and then an anticoagulant can be placed in the stagnant blood or can elute from the valve 160.

A common actuator assembly 95 may be coupled to each valve, in particular when they are configured to turn "on" or "off" together at the same time; or, such common actuator assembly 95 may be adapted to individually actuate at separate instances or intervals. Moreover, independent actuators may be employed.

System 100 may be further modified to have only one valve 150 within the fistula 110, as illustrated by way of example by the embodiments shown in FIGS. 4A-D.

Figure 4A:
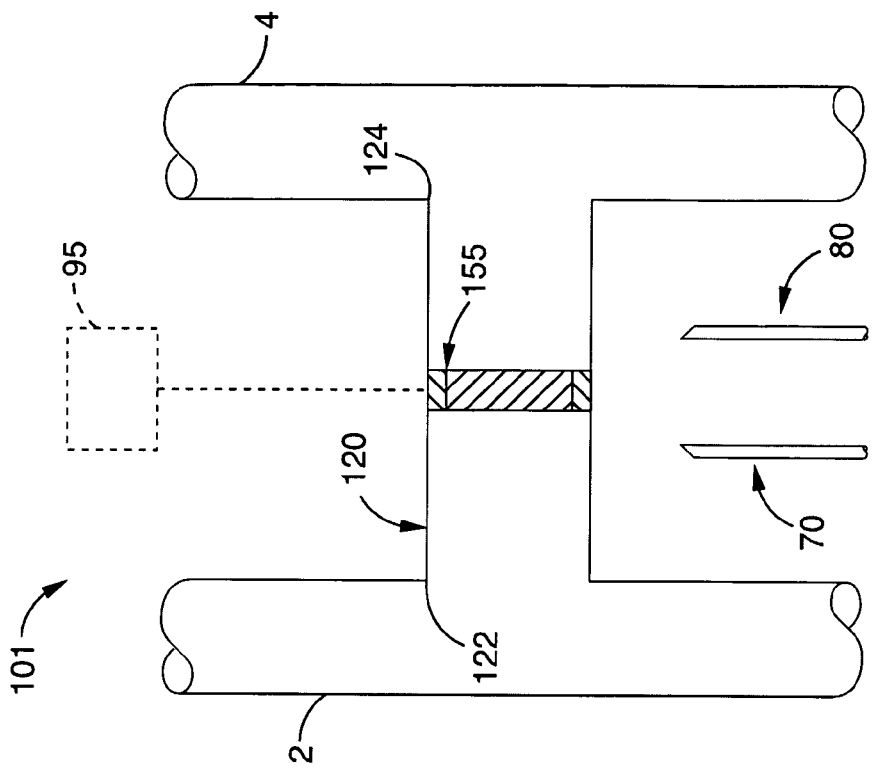
FIG. 4A shows a similar schematic view of the same anatomy to that shown in FIGS. 1A-D and FIGS. 3A-C, except shows another hemodialysis system according to the invention with a single valve coupled to an AV-fistula lumen at a location between the vessel anastomoses at the AV-fistula's ends.
Figure 4B:
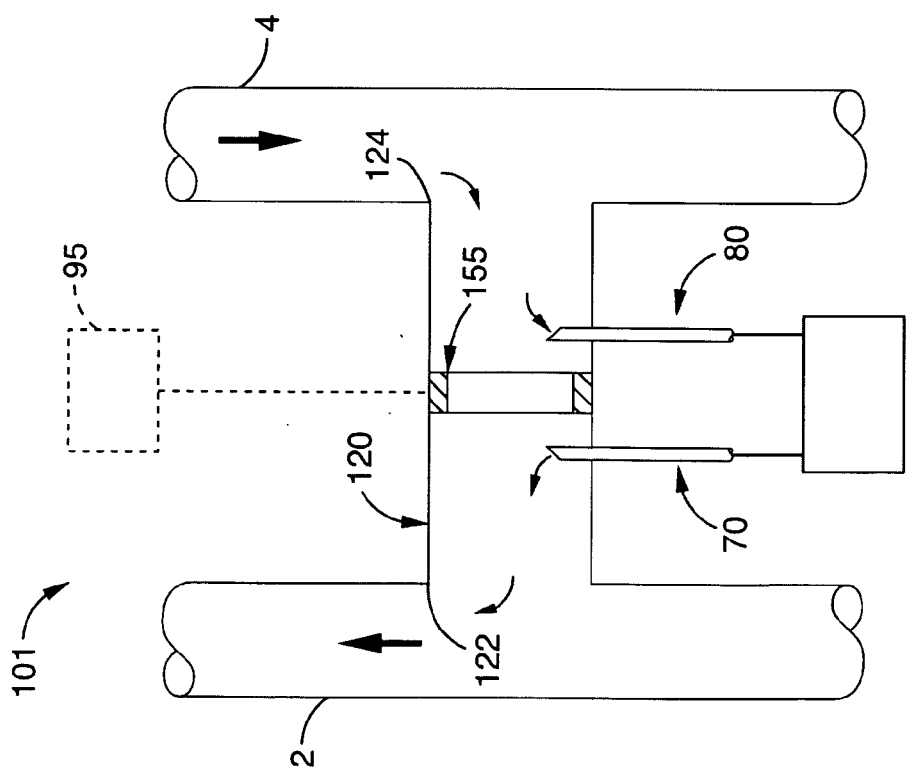
FIG. 4B shows a similar schematic view of the same anatomy and hemodialysis system as that shown in FIG. 4A, except shows the system in another mode of use with the centrally located valve adjusted to an off position that corresponds to a substantial blockage of blood flow between the artery and vein along the fistula.
Figure 4D:
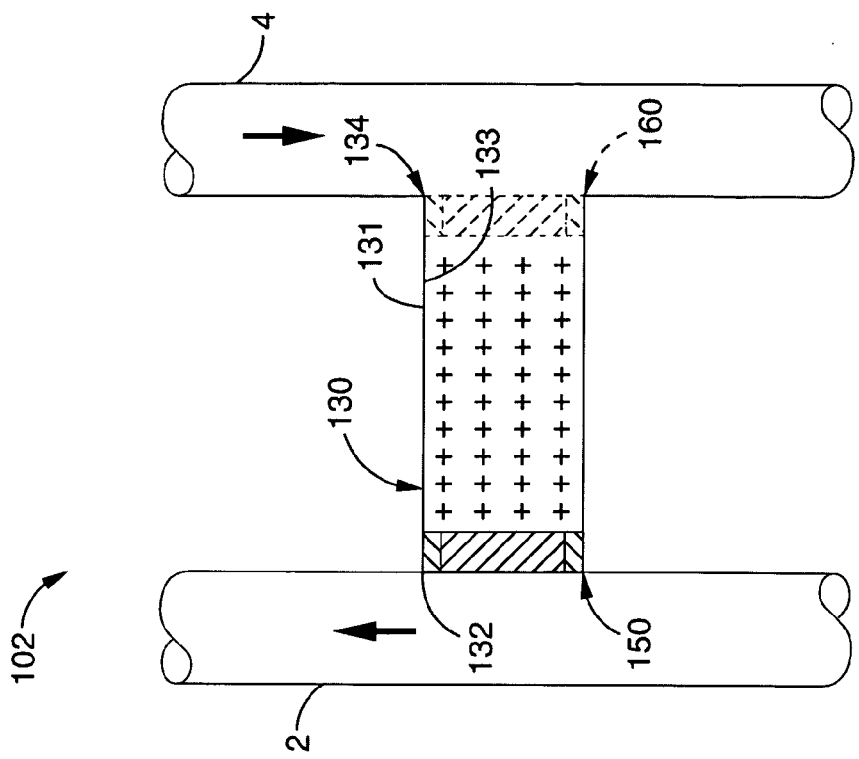
FIG. 4D shows a similar schematic view of the same anatomy and system as that shown in FIG. 4C, except shows the system in another mode of use with the valve assembly closed, the hemodialysis needles removed, and a static field of fluid located within the fistula.

More specifically, system 101 in FIGS. 4A-B provides an embodiment wherein valve assembly 155 is located substantially in a central region of fistula 110 between vein 2 and artery 4, which central valve 155 is shown open in FIG. 4A and closed in FIG. 4B. In this configuration, the ability to purge the fistula 120 from blood during "off" periods is generally lost. However, the benefit of flow cessation of the shunt through the fistula 120 is retained, and the blood resident on either the venous or arterial side of the valve 150 only occupies an area of about one-half the length of fistula 120, each end 122, 124 being adapted to mix with the adjacent flowing vessel.

Figure 4C:
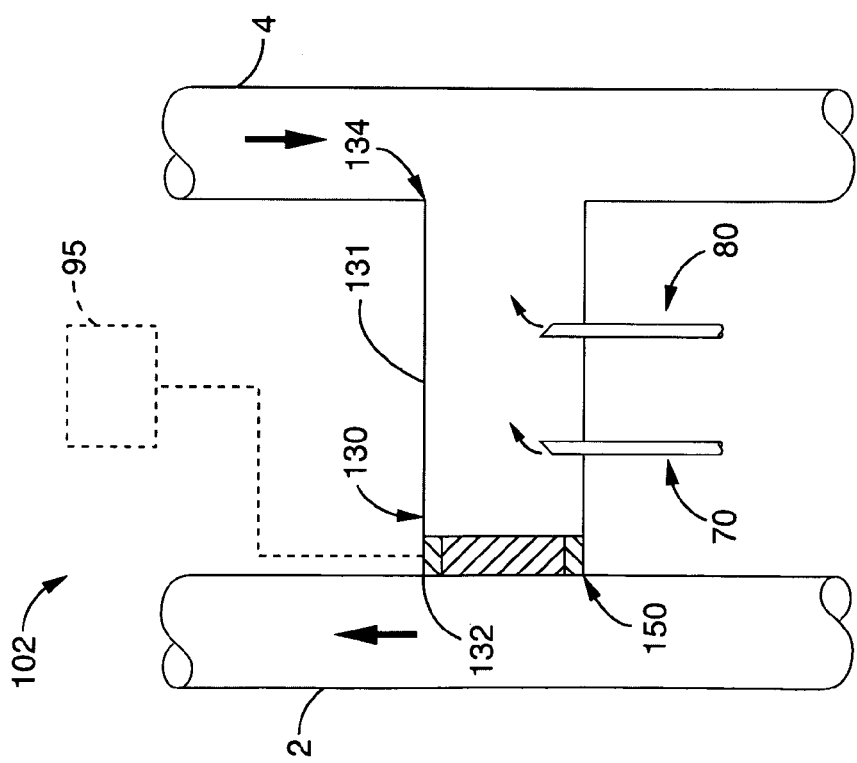
FIG. 4C shows a similar schematic view of the same anatomy as that shown in FIG. 4B, except shows a modified system and mode of use wherein the valve assembly associated with the AV-fistula is located along a region of the fistula that more closely corresponds to one of the artery or vein than the other.

A valve 150 having a position along only one anastomosis site, such as the venous side 132, is shown in FIGS. 4C-D. After dialysis is finished, the valve 150 on the venous side 132 of fistula 130 is closed and the fistula 130 is flushed using one or both of needles 70, 80 with a solution such as a fluid agent, which may contain for example an antithrombotic solution and/or a pharmaceutical inhibitor of neointimal hyperplasia, or other diagnostic or therapeutic agents as elsewhere herein described. In the interim between dialysis sessions, flow proceeds in the normal physiologic direction and the graft is essentially a column of stagnant anticoagulated fluid waiting to be used again. As mentioned above and shown in shadow in FIG. 4D, if there is a second valve 160 at the arterial anastomosis side 134, then this valve is turned off after the flush as well, isolating the fistula contents from blood until the next procedure.

Fistula valves according to the embodiments in FIGS. 3A-4D can be placed at the time of fistula creation (both artificial and native vessel fistulas), or placed into an artificial vessel prior to implantation. Seating regions built into a graft wall that makes up a fistula may be built for example to interface with and permanently receive and house a detachable valve that might be delivered into the fistula translumenally or otherwise. Or such valves themselves may include a mechanism to allow for in-situ positioning and implantation within the fistula graft, such as by piercing hooks or other fasteners for example that might extend around a circumferential annulus surrounding the valve, and which may be adjustable from a retracted position for delivery to the location within the fistula, to an extended position for engaging the fistula graft wall to form the final integrated implant assembly.

Various different appropriate mechanisms may be used for valves 150 or 160, as would be apparent to one of ordinary skill. In one embodiment, one or both of valves 150, 160 are electromechanically activated. When the dialysis access technologist is to initiate dialysis, the valves are actuated. According to another embodiment the valve is adapted to be ferromagnetically actuated, such as by including a ferromagnetic material in the presence of an adjustable magnetic field actuator. The apparatus is moved passively at the time of dialysis with an external electromagnetic actuator. The valve then is turned from the off position to the on position via magnetic actuation and dialysis commences.

Figure 5A:
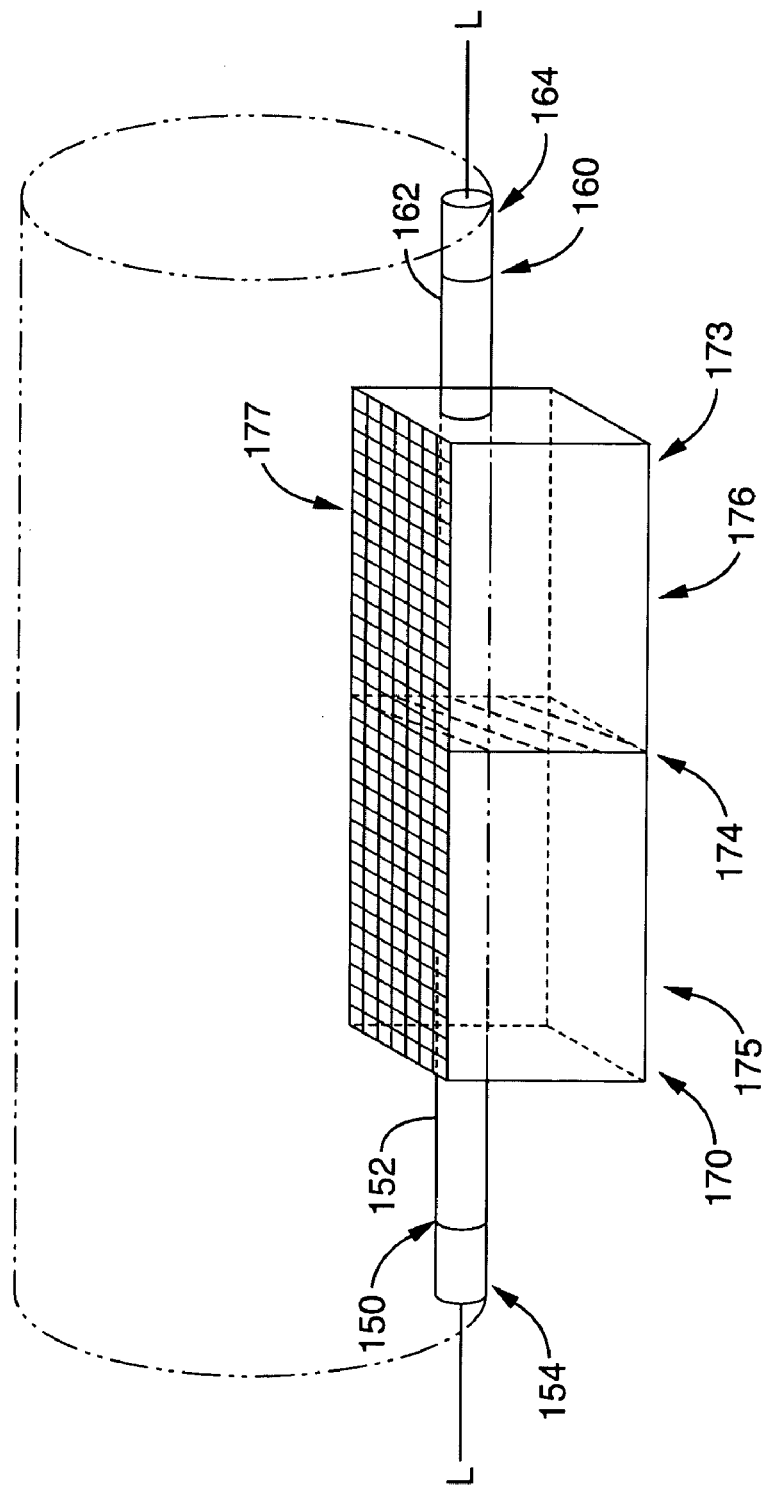
FIG. 5A shows an angular perspective view of one embodiment for a valve assembly that is adapted for use in a hemodialysis system such as the system shown in FIGS. 3A-C, and shows the valve assembly with both valves in an open condition similar to that shown in FIG. 3A with respect to a reference AV-fistula shown in phantom.
Figure 5C:
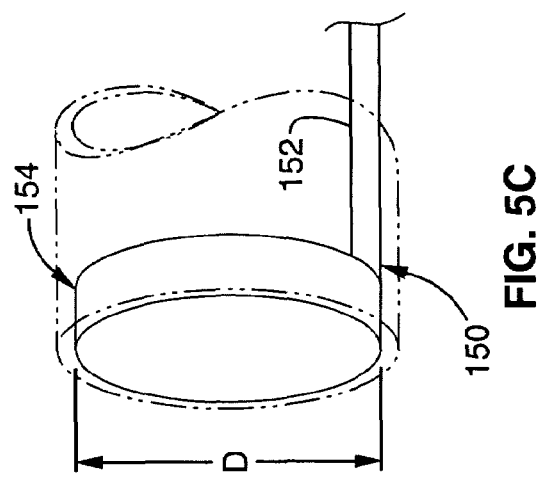
FIG. 5C shows an exploded side view of the valve shown in FIG. 5B, but shows the valve in the closed condition with respect to the anastomotic region of the AV-fistula shown in phantom.
Figure 5B:
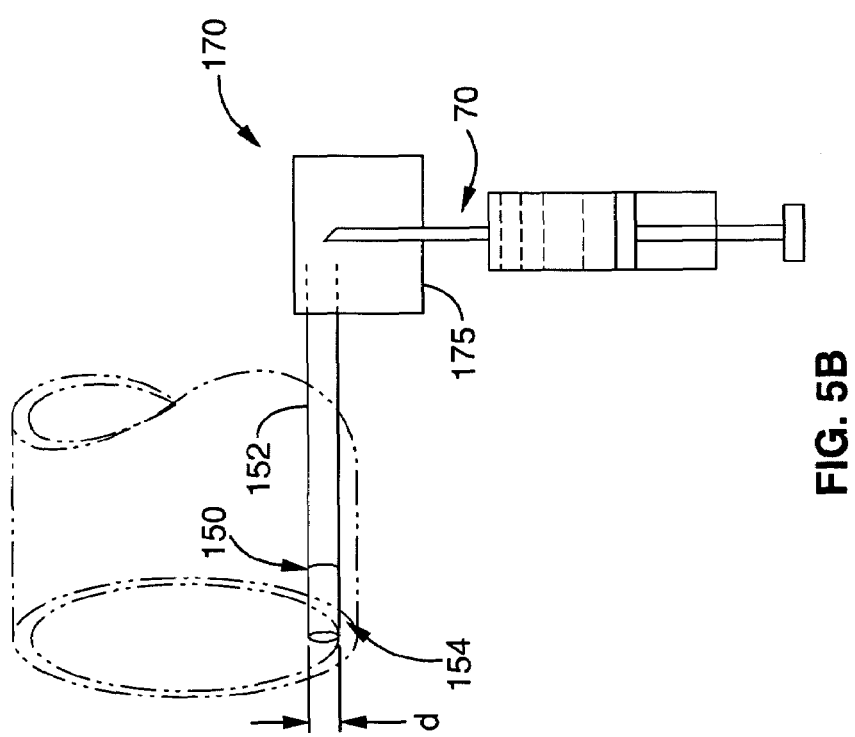
FIG. 5B shows an exploded side view of one valve of the valve assembly shown in FIG. 5A in the open condition with respect to one anastomotic region of the AV-fistula shown in phantom.

A further example of this embodiment is illustrated in FIGS. 5A-C and uses hydraulic actuation for valves 150, 160. More specifically, valve system 170 includes a valve assembly 173 opposite valve assembly 177 of similar construction and arranged in a similar manner to valve system 50 shown in FIGS. 1B-1D. However, valve system 170 includes a wall 174 that isolates valve system 170 between a first portion 175 and a second portion 176. First portion 175 is fluidly coupled to valve 150 via elongate tubular member 152; second portion 176 is fluidly coupled to valve 160 via elongate tubular member 162. Each of valves 150, 160 includes an expandable member 154, 164, respectively, that is adjustable between a radially collapsed condition and a radially expanded condition relative to the longitudinal axis L of the respective elongate tubular member. As shown for illustration with respect to valve 150 in context to a reference AV-fistula graft in shadow in FIGS. 5A-B, expandable member 154 has a diameter d adapted to allow blood flow to pass thereover, such as during hemodialysis procedure using needles through valve system 170 in a similar way previously described for valve system 50. In the radially expanded condition shown in FIG. 5C, however, expandable member 154 has an expanded outer diameter D that is greater than collapsed diameter d and is adapted to substantially occlude flow through the reference fistula. This diameter D may be equal to, slightly less than, or slightly greater than the general inner diameter of the graft fistula in order to achieve the desired substantially occluded result.

Expandable members 154, 164 in one highly beneficial embodiment are inflatable balloons, and may be highly compliant or elastomeric, such as latex, polyurethane, or silicone, or may have relatively less compliance or elasticity and assume a memory fold geometry (not shown) in the collapsed condition. In the compliant variation, the material forming the balloon skin preferably has an elastic elongation of at least 500% before reaching the outer diameter D, and may be up to about 700 to about 900% elastic elongation, in any event optimized to preserve low profile within the graft lumen during the collapsed condition for optimal blood flow. The balloons are inflated with pressurized fluid from a needle into the chamber(s) of valve system 170, and remain inflated upon removal of the needle as there is an external seal at valve assembly 173 in a similar manner to that described for fluid agent delivery via valve system 50 in FIGS. 1B-D.

A grating valve structure similar to grating 60 in FIGS. 2A-D may be utilized for the present embodiment of FIGS. 5A-C, wherein the grating is designed to allow for sufficient fluid pressure retention within the chamber of valve portions 175, 176 to allow for inflation of balloons at 154, 164 via pressure injection from needles into portions 175, 176. Moreover, these independent valve portions 175, 176 allow for independent control over valves 150, 160. This is shown for example in FIG. 5B with needle 70 injecting fluid into portion 175 of valve system 170. Though, alternative embodiments contemplate a more unitary chamber construction with one common fluid actuation.

In either the embodiments shown schematically in FIGS. 3A-C, 4A-B, or 4C-D, a significant benefit is provided to the patient by not having a blood-shunting fistula when not on dialysis. The conventional fistula per se has its own morbidity. It increases circulating volume and cardiac output by 20%, thus straining the heart. Furthermore, many patients complain of a steal syndrome to their hands in which too much blood is shunted away from their hands, leading to ischemia. Moreover, neointimal hyperplasia may also be thwarted at the anastomotic sites because there is no flow most of the time. The risks and extent of these potential problems are reduced by these embodiments of the present invention.

Drug Eluding AV-Fistula Graft

A further embodiment of the invention is provided in FIGS. 6A-7B, wherein certain aspects of an AV-fistula are specially adapted to prevent neointimal hyperplasia associated with chronic implantation, and in particular with respect to the respective venous and arterial anastomosis sites, and still more particularly with respect to venous anastomosis site.

Figure 6A:
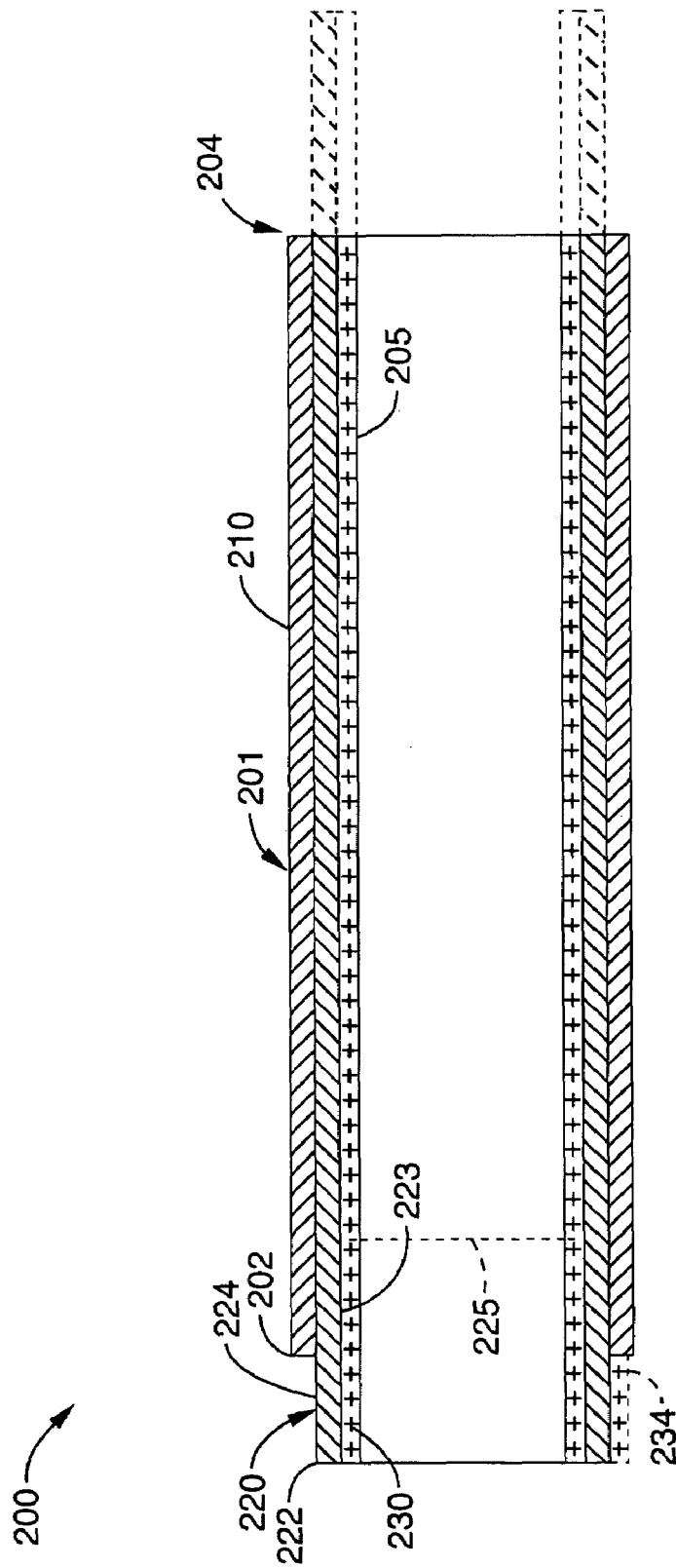
FIG. 6A shows a longitudinally cross-sectioned view of a further AV-fistula embodiment according to the invention.

More specifically with respect to the embodiment shown in FIG. 6A, an AV-fistula 200 includes an elongated body 201 with an outer graft member 210 that is shown coaxially disposed around an inner liner 220. Outer graft member 210 defines an inner lumen 205, and may be constructed of similar design and materials as standard AV-fistula graft materials.

Inner liner 220 extends beyond at least one end of outer graft member 210 and terminates at an end 222 that corresponds to end 202 of AV-fistula. Inner liner 220 may also extend within outer member 210 all the way to the other end 204 of body 201 and outer member 210. Or, inner liner 220 may terminate beyond the other end 204 of outer member 210. Still further, inner liner 220 may terminate within outer member 210, such as is shown at end 225, which may be for example a point of attachment between liner 220 and outer member 210, leaving the rest of inner liner 220 "free floating" within outer member 210.

In any event, inner liner 220 where it extends from the end 202 of outer member 210 is adapted to form a seal over the anastomosis area between outer graft member 210 and the corresponding vein or artery. This seal is adapted to prevent significant exposure to blood factors within the vessel to the anastomosis area, which is predicted to result in prevention of neointimal hyperplasia that has otherwise been observed to occur at such anastomoses. In the event inner liner 220 extends beyond only one of the ends 202, 204 of outer graft member 210 for such purpose, this would typically be located along the venous anastomosis end when placed in-vivo, since this is the site for most frequent occurrence of the hyperplasia condition.

Inner liner 220 is generally more flexible, and typically much more flexible, than the outer graft member 210, such that pressure from blood flow acts to effectively "stent" the liner 220 against the wall to form the desired seal across the anastomosis. In one particular mode, the liner 220 is a membrane of flexible material, and is substantially thin and shaped to provide the intended result just described at the desired anastomosis site. The anastomosis is sewn over the membrane. Afterward, the blood flow through the fistula and its associated pressure effectively stent the membrane open against the vein wall.

In addition, inner liner 220 in the embodiment shown in FIG. 6A is also "doped" with a bioactive agent, such as pharmaceutical inhibitor of neointimal hyperplasia or anti-thrombotic, or other agents herein described or apparent to one of ordinary skill. Such agent may be provided as an interior coating 230, per the variation shown, that may extend along the liner length, or be localized to primarily the region of the intended anastomosis site and where liner 220 extends. Such coating may be a direct layer of the agent, which may be in for example solid, gel, or paste form deposited along a surface of the liner 220. Or the coating may include at least one additional coating material to assist in adhesion and desired elution rate of the biologically active agent. A layered structure of members may also provide for a reservoir-type housing to hold the agent that eludes through one of the layers into the desired area. Such agent may also be impregnated, adsorbed, or otherwise incorporated into the membrane. Physical pores or other structures may also be provided along liner 220 to house the agent that then leaches therefrom. In one highly beneficial mode, the device 200 is constructed such that the pharmaceutical inhibitor or other agent is released in a controlled manner over time.

Coating 230 is shown in FIG. 6A along an inner surface 223 of liner 220 for the purpose of illustrating one mode.

However, because neointimal hyperplasia takes place within the vessel wall, the opposite outer surface 224 may also be the location for providing the coating, as shown at coating layer 234.

Thus, according to the foregoing embodiments, neointimal hyperplasia may be prevented in an AV-fistula, and in particular at its anastomosis, and further in particular at the venous anastomosis, by both shielding the anastomosis from turbulent flow, and by slow release of the pharmaceutical.

A further embodiment shown variously in FIGS. 6B-6G provides anastomosis extension or liner 220 with a plurality of longitudinal, circumferentially positioned members or fingers 227 that may be formed for example by cutting slits in an annular tubular member as shown at 220 in FIG. 6A. These slits may extend within the internal lumen of outer body 210, as shown in FIG. 6C, or may be unitary within body 210 for example for better adhesion. Fingers 227 are useful in aiding the ability to position extension member 220 into the lumen of vein 2 during a suturing procedure for anastomosing. As shown in FIG. 6D, a rear suture 240 is completed before a top suture 242. During the suturing process, sutures may be formed between fingers 227, or at the location of slits separating them. The fingers may be placed within the lumen of the vein 2 between each suture, aiding in the ease and accuracy of the process. A final anastomosed end-to-end anastomosis is shown in FIG. 6E for further illustration.

The design of FIG. 6B also allows for side anastomosing, as shown in FIGS. 6F-G. More specifically, the fingers 227 on the "upstream" side of the AV-graft 201 may be removed, such as by cutting them, allowing the downstream side fingers 227 to be positioned to their ends 222 against the inner wall of vein 2 under the pressure of downstream blood flow, as shown in phantom and by aid of a reference arrow showing the deflection under blood flow. In addition to cutting certain of the fingers 227 themselves, their length may also be custom trimmed by the healthcare provider prior to a surgical anastomosis, such that the initial assembly may be provided particularly long to provide for custom trimming to meet most anticipated needs. Further to the embodiment providing only downstream fingers 227, it is also contemplated that an alternative graft to that shown in FIG. 6B may be provided within fingers 227 only on one circumferential aspect of the graft for use in this type of side anastomosing.

Figure 7A:
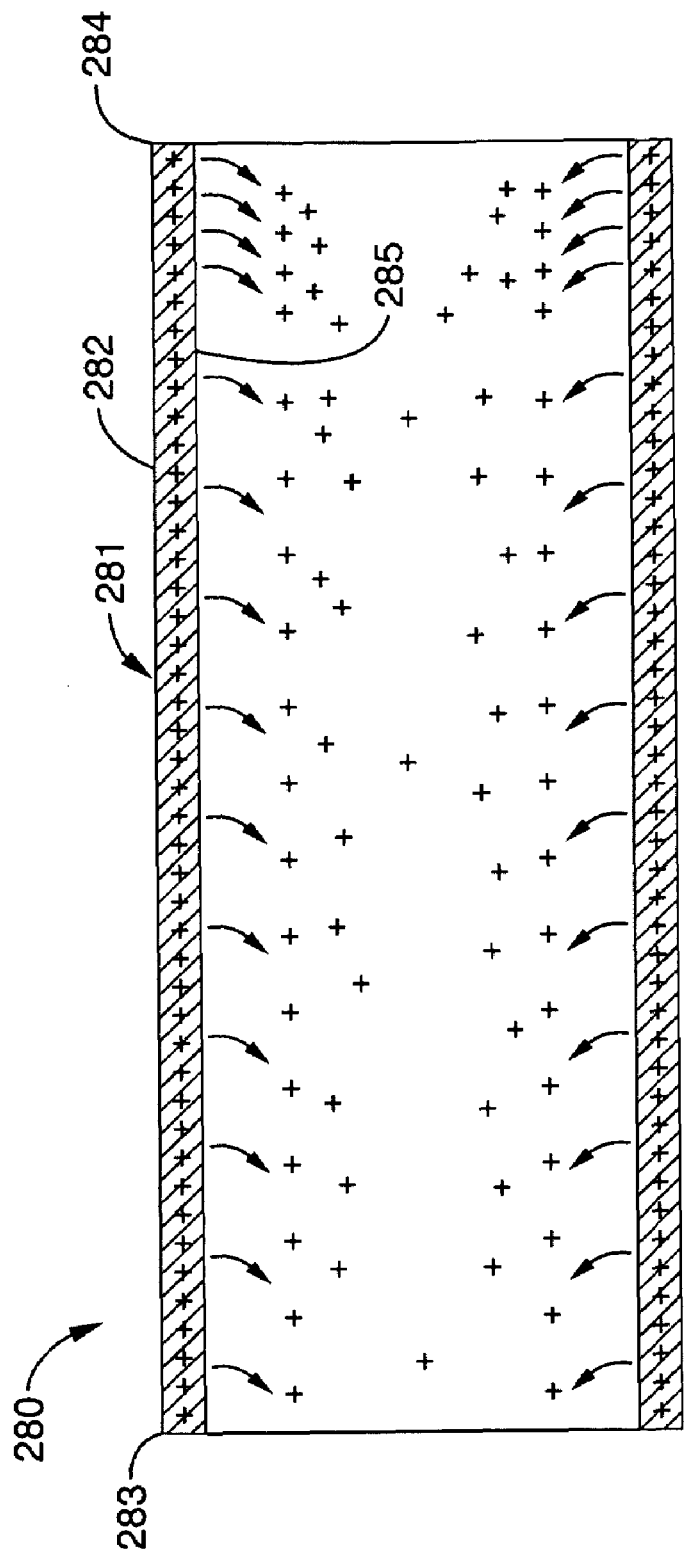
FIG. 7A shows a longitudinally cross-sectioned view of another AV-fistula embodiment of the invention.

In another embodiment of the invention shown in FIG. 7A, an AV-fistula graft 280 includes an elongate body 281 having a graft wall 282 that defines a lumen 285 that extends between ends 283, 284. A pharmaceutical preparation or other biologically active agent is impregnated into the entire graft wall 282 so that the graft itself becomes the pharmaceutical reservoir. The agent is slowly released into the laminar boundary layer of the blood flow through the graft lumen 285, as shown in FIG. 7A by way of small flow arrows. Being approximately stagnant at the edge of the boundary layer, the elution profile for the agent from the graft into that layer may be largely dependent on diffusion.

As also shown, the biologically active agent may also be adapted to elude more aggressively along at least one end 283, 284, where stenoses are most frequently found. This may be done by providing more agent there, such as in higher concentration preparations. Or, the only location that the agent is deposited may be along such ends. Only one end may also provide for the drug elution, which would more often be the venous anastomosis end in use.

A further embodiment is illustrated in FIG. 7B, wherein a separate reservoir 289 is coupled to the graft fistula 280 and is adapted to deliver biologically active agent over prolonged periods of time into the desired regions of the graft. Such reservoir may be located closely adjacent graft fistula 280, such as on or adjacent to an outer surface thereof, or may be more remotely located such as in another area of the body or even externally of the body. The reservoir may also be located and designed in a manner that allows it to be refilled, such as through needle penetration of a sealing membrane or valve, as elsewhere described. In addition, the coupling to the graft may include several paths, such as for example two paths at each of two end portions 286, 288 of the graft fistula 280 where anastomoses are to be formed.

FIG. 7C shows further detail of one further beneficial variation for the embodiment shown in FIG. 7B, and includes an annular fluid bladder 290 associated with an AV-graft body 281. In particular, FIG. 7C shows bladder 290 embedded within graft body 281, and includes a porous wall 291 with a plurality of pores 295 located to infuse drug or other agent internally through the inner aspect of wall 281 and into the respective AV-fistula lumen. A further more detailed view of a bladder 299 having a tubular shape with a length L and a porous inner wall 293 with a plurality of pores 295 is shown in FIG. 7D. Length L, extending between ends 292 and 294, is to be adapted for the particular application, but in general is considered to be optimized to provide the local agent delivery necessary to achieve the intended therapeutic or prophylactic result at an anastomosis region. Bladder 290/299 includes a coupling stem 297 that extends from body 281 and is fluidly coupled to remotely located source 289, which again may be refillable, and may be within the body or externally located.

Bladder 290/299 may be formed from many different suitable materials and according to many suitable methods as would be apparent to one of ordinary skill. In one variation, bladder 290/299 is constructed from a metal ring or tube, such as sealed coaxial metal hypotubes, which metal may be for example stainless steel or a nickel-titanium alloy. In another beneficial variation, the bladder 290/299 is of polymeric construction, such as polyethylene, silicone, polyurethane, hytrel, nylon, or PEBAX™. Suitable exemplary methods for forming such polymeric tube or ring include without limitation a free-blowing or blow molding process, or other form of molding such as injection molding.

The pores 295 may be discretely formed annular regions in the bladder wall, such as by laser drilling, mechanically drilling, electronic discharge, or other suitable post-processing techniques. The dimensions of the pores may be variable, and may depend for example on the molecular weight or viscosity of the agent to be delivered, delivery profile desired. Or, they may be variable within a particular bladder itself to achieve variable delivery over different areas, e.g. more aggressive delivery closest to the ends. Nevertheless, for the purpose of illustration, suitable embodiments provide the pores with diameters between about 0.1 mm to about 1 mm, and may be about 0.5 mm for certain applications. Alternatively, the membrane forming bladder 290/299 may be a "micro" porous material, such as certain suitable known forms of PTFE. One such suitable material process for example provides PTFE with a network of interconnected microfibrils with gaps therebetween. The gaps are filled with a material that may be controllably removed by exposure to a solvent. According to the present embodiment of the invention, by providing the solvent process only along the surface intended to be the internal surface of the bladder 290/299, the internally pored structure may be achieved without providing leaking pores along other circumferential regions of the bladder 290/299 (thus isolating the agent delivery only to the internal lumen). Or, it should be further appreciated that the localized interior porosity is a beneficial variation but not always necessary, and porosity may be provided elsewhere including all locations along bladder 290/299 with respect to graft member 281.

Bladder 290/299 may be positioned internally within or externally around graft wall 281, depending upon the particular application (see, e.g., FIGS. 7C and 7D, respectively), and need not be embedded therein. In this regard, bladder 290/299 may be provided in combination with graft body 281 by a manufacturer, such as in a pre-packaged sterilized assembly. Alternatively, bladder 290/299 may be provided separately for final assembly by an end user prior to a surgical anastomosis. However, the embedded variation is considered highly beneficial for chronic implantation in a blood field.

Energy Treatment of AV-Fistulas

The present invention also provides for highly beneficial system and method for coupling energy to regions of implanted AV-fistula grafts, such as at their anastomoses, in order to prevent or otherwise treat formation of occlusive stenoses. In particular, such systems and methods are adapted to provide such energy coupling by use of passive treatment assemblies positioned along the AV-fistula graft that are actuated by exposure to an externally applied energy field. This allows for routine maintenance treatments with significantly reduced costs and complexity to other previously disclosed invasive systems that require active energy delivery sources to be introduced into a fistula during each time for energy treatment. Therefore, maintenance may be done more frequently for more efficacious prevention. In addition, the present systems and methods provide for prevention of both neo-intimal hyperplasia, as well thrombus formation or adhesion to grafts or their anastomosed vessels. The treatment assembly may be provided on a disposable delivery platform, whereas the remote energy source for applying the actuating field may be an implant or otherwise reusable, in particular for embodiments that allow for transcutaneous application of the actuating energy field. The treatment assembly not requiring an active energy source is also adapted to be made sufficiently small and flexible to be delivered into a lumen of a graft for treatment through a hemodialysis needle. Further aspects of these benefits will be further appreciated by reference to more detailed descriptions of the particular exemplary embodiments as follows.

Figure 8A:
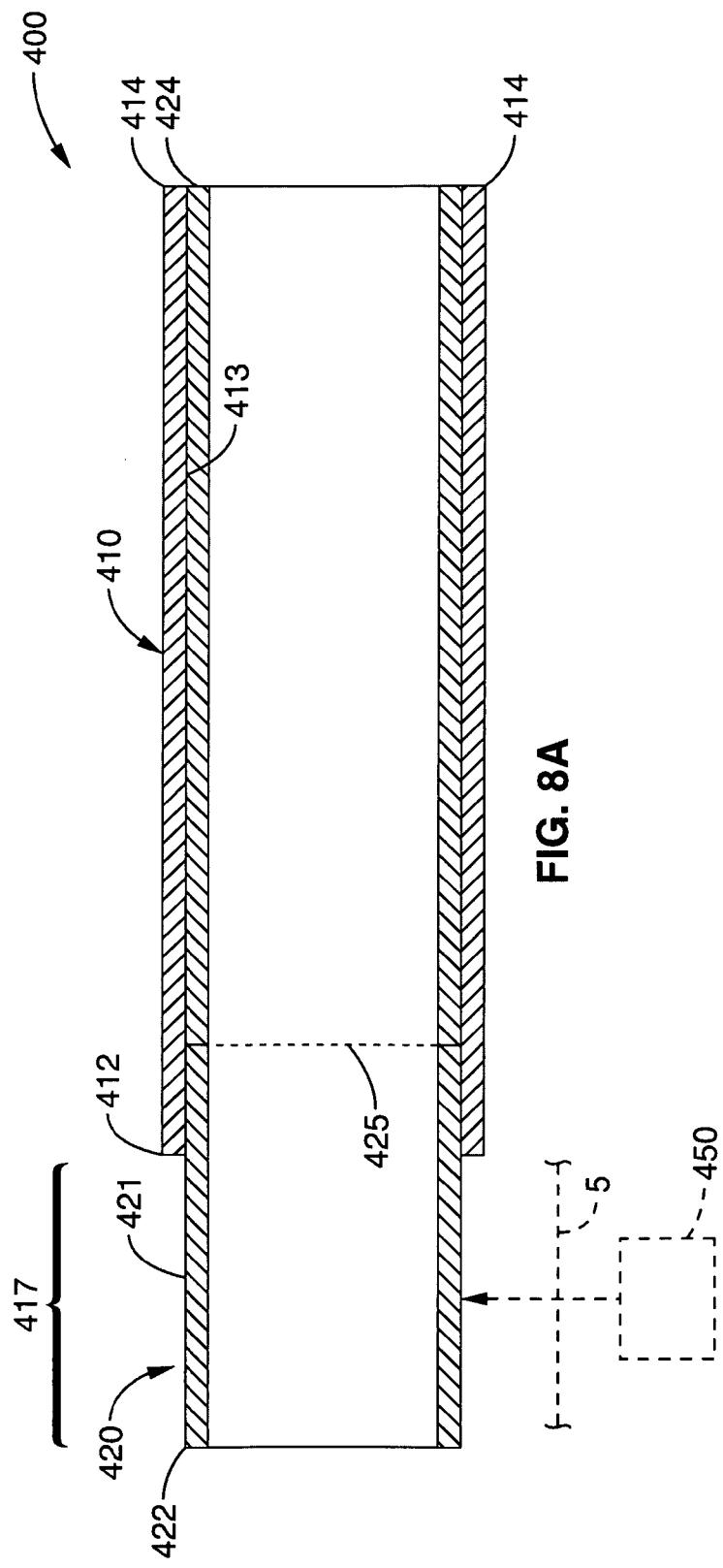
FIG. 8A shows a further embodiment with an AV-fistula and a remotely located energy source, shown in shadow, and energy is shown schematically coupled between an end of the AV-fistula and the remotely located energy source across a tissue barrier such as the patient's skin.

One particular beneficial embodiment related to this aspect of the invention is shown in FIG. 8A as follows. A hemodialysis system 400 is provided with an AV-fistula 410 that is constructed and operated in a manner such that energy may be coupled between the fistula 410 and an area adjacent thereto. This coupled energy is adapted to prevent or remove stenosis, such as thrombus or neointimal hyperplasia.

An energy source 450 is provided that transduces a first energy field to a treatment region 417 of the graft 410, which transduction is generally across a skin layer 5 wherein the energy source 450 is located externally of the body (though may be done more invasively, such as by an implanted energy source). This energy is then coupled by the fistula 410 to the surrounding area, typically at a location intended to disturb the growth of neointimal hyperplasia on a regular basis so as not to allow it to form, or to inhibit thrombus formation or adhesion. Or the energy coupling may be performed more acutely in order to remove either or both components of stenosis.

The treatment region 417 is generally incorporated into graft 410 and is adapted to be implanted therewith at the time of surgery, and the can be placed anywhere along the graft 410 but preferably at an intended anastomosis region, most preferably at least at the intended venous anastomosis region, where problems occur after implantation of the graft.

In one embodiment, the treatment region 417 includes a material, such as a coating, which absorbs a specific wavelength of light. For example, a UV-absorbing material may be used in conjunction with an energy source 450 that is a UV light source. Or, infrared light absorbance may be provided in an additional or alternative mode. The material coating can be attached to a flexible material which then extends from the graft, covering the inside portion of the graft fistula 410, such as is shown at inner liner 420 secured to inner surface 413 of graft body 410 and extending from end 412 of outer graft body 410 to terminal end 422. Inner liner 420 is thus similar in arrangement to inner liner 220 in FIG. 6A with respect to the corresponding graft body. This arrangement therefore places the treatment region 417 along a covering to an anastomosis, as well as combines the benefits of such a covering as described above. As described before for such a liner, the treatment region 417 may extend elsewhere along the graft, such as to end 424 corresponding to end 414 of graft 410, or terminate within an interior region such as at end 425.

However, the present embodiment benefits from energy coupling rather than localized fluid agent delivery under the previous embodiment. Further acceptable variations that may assist in such energy coupling include metallic material such as stainless steel or nickel-titanium foils, or fine wires or wire meshes. Further variations include combination of nickel titanium and/or stainless steel and a flexible material polymer such as silicone or PTFE, and can comprise PTFE or silicone or other polymeric membrane doped with ferromagnetic particles or drug releasing particles.

Figure 8C:
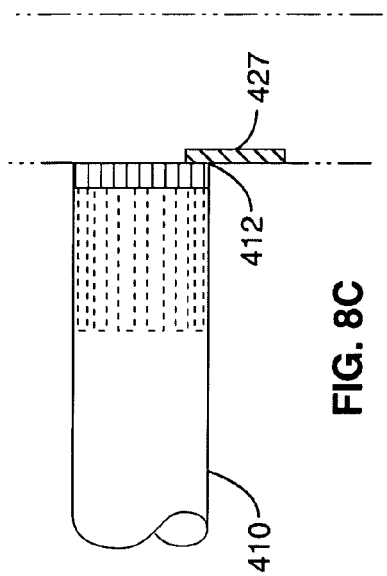
FIG. 8C shows a schematic side view of a further AV-fistula embodiment that includes various aspects of the embodiments shown in FIGS. 8A-B after a completed side anastomosis to a vein shown in phantom and during one mode of use in conjunction with a remotely located energy source.
Figure 8D:
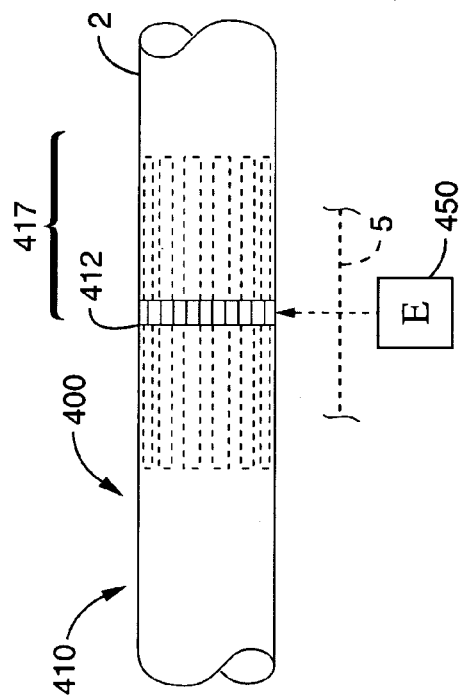
FIG. 8D shows a partial, side perspective view of another AV-fistula embodiment that also includes various aspects of the embodiments shown in FIGS. 8A-B after a completed end-to-end anastomosis to a vein and also during one mode of use in conjunction with a remotely located energy source.
Figure 8B:
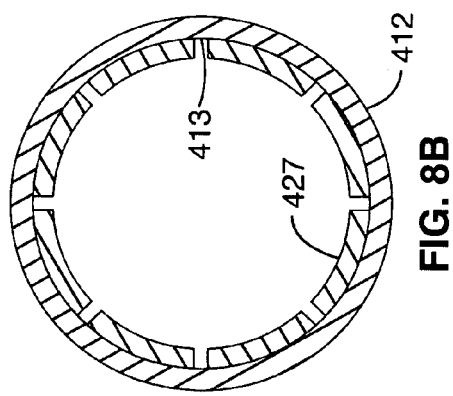
FIG. 8B shows a transverse cross-sectioned view through an anastomosis region of a further AV-fistula embodiment that combines various aspects of the embodiments shown in FIGS. 8A and 6B-D, respectively.

The material chosen for liner extension 420 according to one beneficial variation is flexible and may have several longitudinal slits forming fingers 427 therein in a similar manner to that previously disclosed above by reference to FIGS. 6B-G, such that when blood flows through it, the material is stented against the vessel wall. Various more detail of the arrangement of such fingers according to the present embodiment is shown in FIG. 8B, and in FIG. 8C in the context of a side anastomosis, and in FIG. 8D in the context of an end-to-end anastomosis. FIG. 8D also shows energy source 450 schematically coupled across skin layer 5 to treatment region 417 for the purpose of further illustration, and similar coupling is contemplated for the side anastomosis in FIG. 8C though not shown for simplicity.

The specific embodiment shown in FIGS. 8A-D provides the treatment region 417 along an inner liner extension 420 similar to that described above with respect to FIGS. 6A-B, In another embodiment, the treatment region 417 extending from the end 412 of the graft 410, again preferably near the intended venous anastomosis, contains a ferromagnetic material which is responsive to an electromagnetic energy source 450 from above the surface of the skin of the patient. After or during dialysis, the technician applies the energy source to the region of the anastomosis, causing a rapid mechanical vibration of the material. The vibration prevents or disturbs the occurrence of neointimal hyperplasia at the site.

In general, when the treatment region 417 is warmed at the region of the anastomosis, neointimal hyperplasia is inhibited or disturbed. This procedure would generally be done at the time of dialysis after or during a run three times a week and is meant to prevent neointimal hyperplasia.

It is to be appreciated that in the embodiments just described or other variations therefrom that may become obvious to one of ordinary skill, the treatment region 417 may provide the prophylactic or remedial energy coupling into the surrounding area by heating that area, such as from warming due to the energy coupling to the treatment region 417 from the energy source. However, other energy coupling modes are contemplated as well according to other mechanisms known in the art, such as for example by use of fluorescence provided by the material along the treatment region 417, or otherwise.

A further highly beneficial embodiment is variously illustrated in FIGS. 9A-D. According to this embodiment, a system 500 is provided that also allows for energy coupling between a treatment device and an area associated with an implanted AV-fistula 510. However, according to this highly beneficial embodiment, a separate catheter device 550 is used to achieve the energy coupling during periodic, less-invasive introduction into the fistula lumen 513.

Figure 9A:
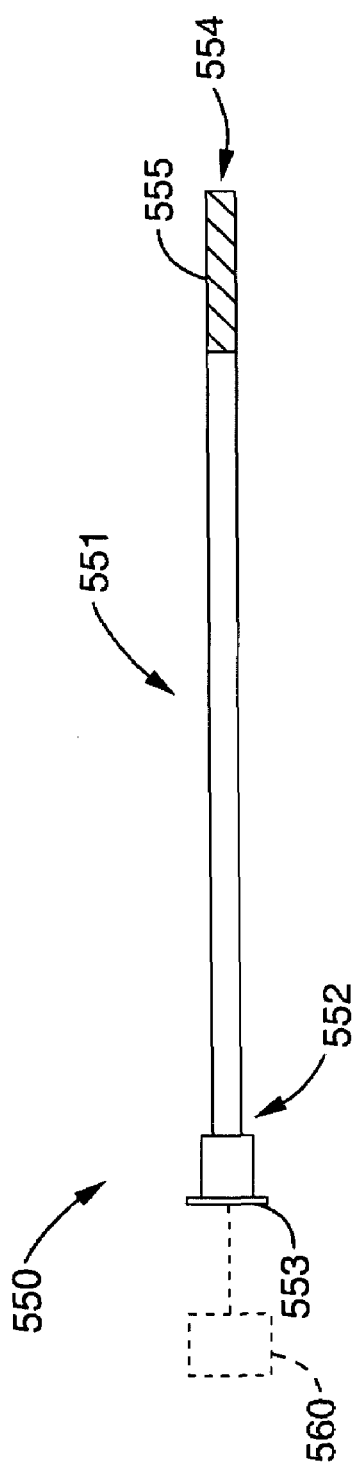
FIG. 9A shows a schematic view of a catheter device embodiment of the invention.

Catheter device 550 is shown schematically in FIG. 9A, and includes an elongate body 551 that extends between a proximal end 552 and a distal end 554. A treatment assembly 555 is located along distal end portion 554. Treatment device 555 is adapted for use in coupling the highly beneficial therapeutic or prophylactic energy within an AV-fistula 510 according to the invention as follows.

Figure 9C:
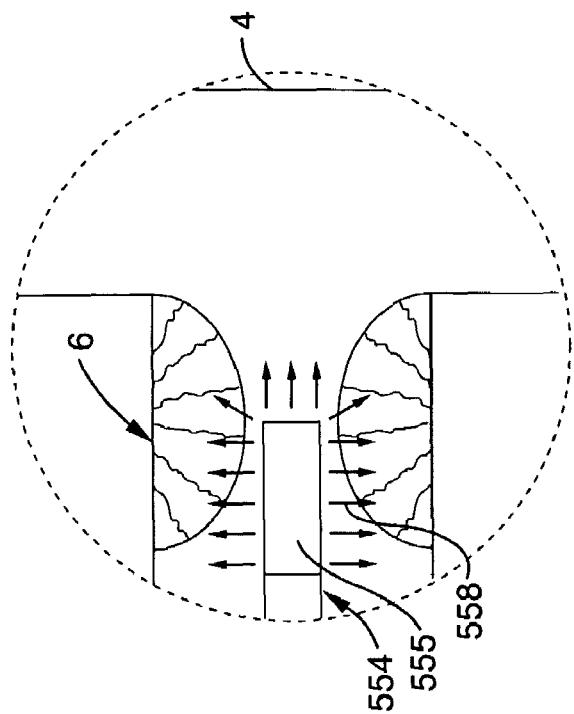
FIG. 9C shows an exploded view of an area of the AV-fistula shown in FIG. 9B being treated by a distal treatment assembly of the catheter device.
Figure 9B:
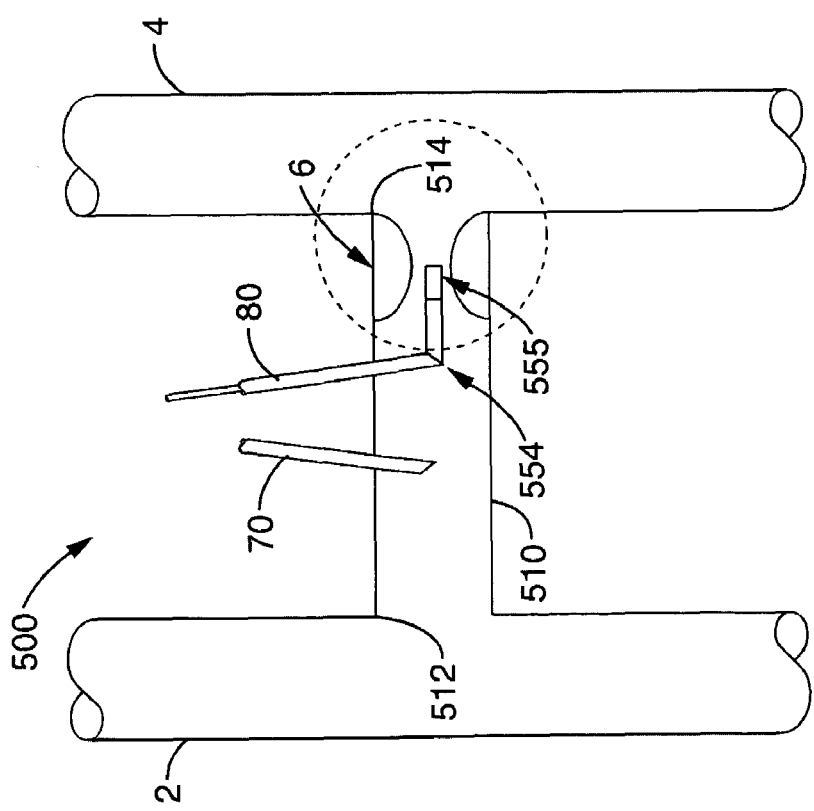
FIG. 9B shows a schematic view of another hemodialysis system of the invention that includes the catheter device shown in FIG. 9A, and shows the system during one mode of use in treating an AV-fistula connecting an artery and a vein.

Referring to FIG. 9B, a typical dialysis system 500 and procedure is depicted, in the sense that an AV-fistula 510 is shown extending between anastomosis sites at its ends 512, 514 with a vein 2 and an artery 4, and further with respect to hemodialysis needles 70,80 being located within the fistula 510. However, FIG. 9B further illustrates an initial mode of using catheter device 550 of this embodiment as follows.

Distal end portion 554 of catheter 550 is constructed of appropriate dimension, design, and material such that it is adapted to be advanced through a dialysis needle 80 and into lumen 513 of fistula 510 such that treatment assembly 555 is located adjacent to the area to be treated with applied energy. Therefore, distal end portion 554 is dimensioned to fit within typical dialysis needles that are generally between about 16 and about 18 Gauge or have an inner diameter between about 1.5 and about 1.0 millimeters. Accordingly, distal end portion will typically have an inner diameter that is no larger than those needle inner diameters, and more preferably provide at least 0.005" clearance within those bores. In addition, the treatment assembly 555 is constructed of appropriate design and material to have appropriate flexibility (or conversely stiffness) to be appropriately positioned in the manner described within the graft 510. Polymeric materials such as polyethylene, nylon, PEBAX™, polyurethane, copolymers, or the like, or combinations thereof or composite constructions therewith, may be suitable materials for forming body 551 at least along distal end portion 554. In addition, body 551 proximally of treatment assembly 555, may be made relatively less flexible with greater stiffness, allowing for advancement through a tight tolerance within a needle.

Still further, distal end portion 554 may be made trackable within graft lumen 513. This may be accomplished by providing a guidewire lumen (not shown) through body 551 that is adapted to slidably engage and track over a guidewire that may be first positioned along the area for treatment. In another variation, distal end portion 554 may also be articulated, such as by providing a pull wire secured to the distal end 554 and that is retractable through a lumen in body 551 by proximal manipulation outside the body, such as via a coupler shown schematically at coupler 553. Other articulation or tracking mechanisms may be suitable as would be apparent to one of ordinary skill.

In any event, as shown in further detail in the exploded view in FIG. 9C, treatment assembly 555 is positioned at a location where a stenosis 6 has developed at an end 514 of fistula 510 that is anastomosed to vessel 4, such as at a vein stenosis. Treatment assembly 555 is then activated to couple an energy field 558 to the surrounding area that includes stenosis 6. By supplying the appropriate energy, stenosis 6 is reduced, which may be by any appropriate mechanism, such as for example without limitation by: ablation, destruction, removal, destruction, desiccation, shrinkage, or expansion or dilation. Mechanical energy may be an appropriate form of energy coupling in some circumstances. However, in highly beneficial aspect of the invention non-mechanical energy coupling is contemplated, such as for example thermal energy, light energy, electrical energy, magnetic energy, etc. Moreover, treatment assembly may emit energy, such as light, thermal, or electrical current. Or, cryogenic coupling may be used, such as by actively cooling treatment assembly 555 in order to cool the surrounding stenotic area by removing thermal energy therefrom.

In a highly beneficial, preferred mode shown in FIG. 9D, a remote energy source 580 is used to first couple energy to treatment assembly 555, which may be in the mode shown across a skin layer 5 of the patient, and may be in a still further preferred mode thermal, light, or inductive energy coupling through the intervening tissues and without requiring "hardwired" coupling to the treatment assembly 555. This allows for significant simplicity of use, wherein the energy source 580 is placed against or next to the skin closest to the treatment assembly 555 below and is activated to couple the energy needed. After receiving the energy, the treatment assembly then is activated to undergo energy coupling to the surrounding area, such as provided above by warming or fluorescing or reflecting light or otherwise. This energy coupling arrangement is further illustrated by way of radially-extending arrows in FIG. 9D.

The treatment assembly may also include a radially expandable member that is adjustable between a radially collapsed condition with a first outer diameter d and a radially expanded condition having a second outer diameter D greater than the first outer diameter. Such an expandable member 556 is shown schematically in cross-section in the radially expanded condition in FIG. 9D, and further in phantom in the radially collapsed condition designated at 556'. By providing for this radial adjustability, the assembly 555 is adapted to be delivered through a dialysis needle in the radially collapsed condition, and then expanded within the anastomosis to the radially expanded condition. The treatment assembly 555 is adapted to couple the energy to the area surrounding the expandable member 556 in the radially expanded condition. Therefore, a greater area may be treated by the energy coupling around the expanded member 556.

Various types of radially expandable members have been previously disclosed and are suitable for use for member 556 as just described. In one beneficial mode, the member in the expanded condition is adapted to provide a substantially circumferential pattern of energy, such as an expandable annular or tubular member. Of further benefit, the expandable member is an inflatable balloon, and may be coupled for example to a pressurizeable source of fluid, such as via coupler 553 and source 560 shown in FIG. 9A. Such balloon may include a material associated with its balloon wall that couples the required energy as described, or the inflation medium itself may be adapted to provide for such coupling. In one particular such example, the inflation medium is adapted to either heat when exposed to a sonic energy field, or otherwise absorb or transmit such energy in a manner that provides the desired coupling. The energy source 580 thus sonifies the medium that is activated as described. Moreover, internal energy sources may be used within such a balloon, such as ultrasound crystals disposed therein.

The device 550 just described may be adapted for resterilization and reuse after providing the desired treatment, or may be adapted for single-use only. Moreover, while the catheter 510 is herein described by reference to delivery through a dialysis needle, other modes are contemplated, including without limitation delivery through either of the vein or artery anastomosed to the fistula, or transcutaneously and directly into or adjacent to the graft fistula, as would be apparent to one of ordinary skill.

In addition to providing the ability to remedially treat and reduce AV-fistula stenosis, the embodiments just described enjoy the benefit of providing a prophylactic solution to AV-fistula stenosis that may be performed on a maintenance basis. Rather than allowing the access fistula to malfunction before treatment, the system 500 is used at the time of dialysis, e.g. once per week, and using pre-existing needle access site. This disturbs development of hyperplasia along the access fistula, thwarting its development before it begins. In addition, the logistics provided by this system 500 are optimized. For example, a patient does not have to be transported to a specialized angiography or interventional radiology suite for care of the dialysis access. The procedure can be performed if desired just after the patient is undergoing dialysis, and avoids additional punctures of the access fistula that eventually lead to aneurysms or other adverse acute and long-term effects.

According to the various embodiments described above, standard AV-fistula graft materials and designs may be used except where otherwise indicated according to the particular aspects associated with each embodiment. Examples include materials such as polytetrafluoroethylene (PTFE), Dacron™, or other commonly used materials. More specific examples may include grafts of the type commercially available from companies such as GORE™ or IMPRA™ Corporations.

Various modifications may be made to the embodiments by one of ordinary skill without departing from the intended scope of the present invention. For example, the various system, device and corresponding method embodiments may be applied to autogenous or artificial AV-fistula grafts, though one particular type may be shown and described for the purpose of illustrating a particular embodiment. In another example, the various embodiments may be adapted for use in other fistulas or medical lumen junctions other than the AV-fistula grafts herein shown and described without departing from the invention (though clearly the invention provides significant particular benefit for AV-fistula graft applications in hemodialysis). Further more specific examples of such further junctions for use in combination with the present embodiments include without limitation: anastomotic junction between a brachial artery and a basilic vein; and anastomotic junctions at either ends of cardiac bypass grafts. In addition, despite the particular benefits provided for the specific embodiments herein shown and described, they may be combined, or aspects thereof, where appropriate to meet a particular need. For example, various of the graft embodiments shown or described without certain specific valves provided by other embodiments may nevertheless include the valves according to such other embodiments, as may be appropriate for a particular case. In another specific example, fistula valves shown and described by reference to FIGS. 3A-4D may be further modified to provide for energy delivery to surrounding areas as treatment assemblies for similar use in treating anastomotic stenoses as described for treatment assemblies of FIGS. 8A-D. In another more specific example, balloons provided for valve purposes according to FIGS. 5A-C may also provide balloon-based treatment assemblies, in effect combining aspects of the embodiments of FIGS. 8A-D and FIGS. 9A-D. Moreover, where treatment methods or device features are shown or described by reference to a specific location relative to a fistula graft (e.g., at a particular anastomosis site), other locations are contemplated.

In another regard, the invention contemplates each individual device herein described as a beneficial embodiment when taken alone, and should not be considered limited to use or combination with others of the embodiments. Notwithstanding the foregoing, combinations and sub-combinations of the assemblies and methods of the various embodiments are also contemplated as highly beneficial; and thus the various systems and overall procedure methods formed thereby are also contemplated as individually beneficial aspects of the invention. In this regard, other devices such as needles, pumps, syringes, etc. may also be combined to form total systems that may be advantageously packaged or sold together as an overall system for performing dialysis.

The embodiments have also been herein described in relation to their highly beneficial use and adaptation for hemodialysis procedures. However, it is further contemplated that the various devices and methods may be applied to other procedures or systems for use in treating or diagnosing other indications or conditions without departing from the intended scope.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An arteriovenous graft system, comprising:
   an arteriovenous graft having an arterial end and an opposite venous end;
   at least one valve device positioned at the arterial end of said arteriovenous graft; and
   a second valve device positioned at the venous end of said arteriovenous graft;
   wherein said valve device comprises an inflatable balloon in communication with said arteriovenous graft;
   wherein said valve device has a closed position when said inflatable balloon is inflated;
   wherein when the valve device is in the closed position, arterial blood flow into the arteriovenous graft is prevented;
   wherein said second valve device comprises an inflatable balloon; and
   wherein said first valve device and said second valve device substantially prevent blood flow into said arteriovenous graft from either the arterial end or venous end when respective inflatable balloons are inflated.

2. A system as defined in claim 1:
wherein said inflatable balloon of said first valve device and said inflatable balloon of said second valve device each have an annular shape; and
wherein said first and second inflatable balloons are positioned inside the arteriovenous graft and expand to said closed position such that the balloons, when in the expanded condition, engage an internal wall of the arteriovenous graft.

3. A system as defined in claim 1:
wherein each of said valve devices further comprises an injection port in fluid communication with each of said inflatable balloons.

4. A subcutaneous arteriovenous graft system, comprising:
an arteriovenous graft having an arterial end and an opposite venous end;
a first valve device positioned at the arterial end of said arteriovenous graft;
wherein said first valve device comprises:
an inflatable balloon;
wherein said inflatable balloon is positioned so as to prevent blood flow into the arterial end of said arteriovenous graft when inflated;
wherein said inflatable balloon is in communication with a first injection port, and
wherein the injection port is configured to be implanted subcutaneously; and
a second valve device positioned at the venous end of said arteriovenous graft;
wherein said second valve device comprises:
an inflatable balloon;
wherein the inflatable balloon is positioned so as to prevent blood flow into the venous end of said arteriovenous graft when inflated;
wherein the inflatable balloon is in communication with a second injection port.

5. A process for reducing hyperplasia in an arteriovenous graft, comprising:
providing an arteriovenous graft having been subcutaneously implanted in a patient;
wherein said arteriovenous graft comprises:
an arterial end in fluid communication with an artery and a venous end in fluid communication with a vein; and
a first valve device positioned at the arterial end of said graft; and
closing said first valve device at the arterial end of said arteriovenous graft;
whereby blood flow into the arterial end of said arteriovenous graft is stopped;
wherein said arteriovenous graft further comprises a second valve device positioned at the venous end of said graft; and
wherein the process further comprises the step of closing said second valve device after flushing said graft.

6. A process as defined in claim 5:
wherein said first valve device and said second valve device each comprise an inflatable balloon;
wherein said inflatable balloon is positioned inside the ateriovenous graft so as to restrict blood flow through the entirety of said arteriovenous graft when inflated.

7. A process as defined in claim 6:
wherein said inflatable balloon of said first valve device and said inflatable balloon of said second valve device each have an annular shape.

8. A process for reducing hyperplasia in an arteriovenous graft, comprising:
providing an arteriovenous graft having been subcutaneously implanted in a patient;
wherein said arteriovenous graft comprises:
an arterial end in fluid communication with an artery and a venous end in fluid communication with a vein; and
a first valve device positioned at the arterial end of said graft;
closing said first valve device at the arterial end of said arteriovenous graft;
whereby blood flow into the arterial end of said arteriovenous graft is stopped; and
delivering a fluid agent inside the ateriovenous graft when the ateriovenous graft is in the closed condition.

9. A method as recited in claim 8:
wherein said fluid agent is configured to prevent clotting or hyperplasia; and
wherein said process further comprises eluting the fluid agent into the arteriovenous graft.

10. A process for reducing hyperplasia in an arteriovenous graft, comprising:
providing an arteriovenous graft having been subcutaneously implanted in a patient;
wherein said arteriovenous graft comprises:
an arterial end in fluid communication with an artery and a venous end in fluid communication with a vein; and
a first valve device positioned at the arterial end of said graft;
closing said first valve device at the arterial end of said arteriovenous graft;
whereby blood flow into the arterial end of said arteriovenous graft is stopped;
a second valve positioned at the venous end of the ateriovenous graft;
wherein said first valve device and said second valve device each comprise an inflatable balloon;
purging blood out of the venous end of the ateriovenous graft after the balloon has closed the arterial end; and
filling the second balloon to expand upon and engage an internal wall of the ateriovenous graft at the venous end to close off the ateriovenous graft.

11. A method as recited in claim 10, wherein ateriovenous graft is configured to be closed for a time period spanning the entire time between hemodialysis treatments without clotting.

12. A method as recited in claim 11, wherein said time period is at least two days.

13. An arteriovenous graft system, comprising:
an arteriovenous graft having an arterial end and an opposite venous end;
a first valve device positioned at the arterial end of said arteriovenous graft; and
a second valve device positioned at the venous end of said arteriovenous graft;
wherein the first and second valve devices have open and closed positions;
wherein when the first and second valve devices are in the closed position, arterial blood flow is prevented from flowing into the arteriovenous graft such that the graft retains a column of fluid.

14. The system of claim 13, wherein the arteriovenous graft is configured to elute a fluid agent into the column of fluid.

* * * * *